(12) United States Patent  
Felch et al.

(10) Patent No.: US 9,721,452 B2  
(45) Date of Patent: Aug. 1, 2017

(54) HAND-WASH MANAGEMENT AND COMPLIANCE SYSTEM

(71) Applicant: WashSense Inc., Reno, NV (US)

(72) Inventors: Andrew Felch, Palo Alto, CA (US);  
Michael Boyd, Clearlake, CA (US);  
John Bessire, Sunnyvale, CA (US);  
Alex Movitz, Oxford, MS (US);  
Connor Dahlberg, Springfield, MO (US)

(73) Assignee: WashSense, Inc., Santa Clara, CA (US)

( * ) Notice: Subject to any disclaimer, the term of this patent is extended or adjusted under 35 U.S.C. 154(b) by 0 days.

(21) Appl. No.: 14/696,000

(22) Filed: Apr. 24, 2015

(65) Prior Publication Data

US 2016/0314683 A1    Oct. 27, 2016

(51) Int. Cl.  
*G08B 21/24*    (2006.01)  
*G06F 19/00*    (2011.01)

(52) U.S. Cl.  
CPC .......... *G08B 21/245* (2013.01); *G06F 19/327* (2013.01)

(58) Field of Classification Search  
CPC ...... G08B 21/245; G08B 21/00; G08B 21/02; G08B 25/10; G08B 25/22; G06F 19/327; G06K 9/00355; A47K 2210/00; A47K 2005/1218  
See application file for complete search history.

(56) References Cited

U.S. PATENT DOCUMENTS

| | | | |
|---|---|---|---|
| 7,755,494 B2 | 7/2010 | Melker et al. | |
| 2002/0104159 A1* | 8/2002 | Nishioka | E03C 1/057 4/623 |
| 2009/0087028 A1* | 4/2009 | Lacey | G08B 21/245 382/103 |
| 2009/0301523 A1* | 12/2009 | Barnhill et al. | 134/18 |
| 2010/0164728 A1* | 7/2010 | Plost | 340/573.1 |
| 2012/0062382 A1* | 3/2012 | Taneff | 340/573.1 |
| 2015/0119780 A1* | 4/2015 | DeLuke et al. | 602/19 |
| 2015/0127365 A1* | 5/2015 | Rizvi et al. | 705/2 |
| 2015/0169587 A1* | 6/2015 | Silverman et al. | 707/51 |

* cited by examiner

*Primary Examiner* — Laura Nguyen  
(74) *Attorney, Agent, or Firm* — Robert Crownover

(57) ABSTRACT

A method and apparatus for managing hand-washing compliance can include: sensing a user's hand-wash motions; estimating hand-wash scrubs per minute based on the user's hand-wash motions; counting a total hand-wash scrubs based on the user's hand-wash motions; estimating hand-wash vigor based on the user's hand-wash motions; calculating a hand-wash score based on the hand-wash vigor; displaying the hand-wash vigor, the total hand-wash scrubs, and the hand-wash scrubs per minute on a display; and displaying a timer that counts down based on the hand-wash vigor.

20 Claims, 13 Drawing Sheets

HAND-WASH MANAGEMENT AND COMPLIANCE SYSTEM

TECHNICAL FIELD

This disclosure relates to an electronic system for compliance monitoring, more particularly for detecting and encouraging industry compliant sanitization and washing procedures.

BACKGROUND

Tens of thousands of people die each year from infections acquired in hospitals. These "hospital acquired" infections, also referred to as nosocomial infections, are unrelated to a patient's initial hospital admission diagnosis. In the United States, it has been estimated that as many as one hospital patient in ten acquires a nosocomial infection, or 2 million patients a year. Estimates of annual costs related to nosocomial infection range from $4.5 billion to $11 billion and up. Studies have shown that at least one third of nosocomial infections are preventable.

Nosocomial infections due to resistant organisms are an extremely serious problem that threatens the U.S. healthcare system and the welfare of its citizens. Microbes can acquire resistance to antibiotics and anti-fungal and antiviral agents and as the numbers of resistant organisms increase, the number of new antimicrobial agents to treat them has not kept pace. In fact, community acquired nosocomial infections, especially methicillin resistant staphylococcus aureus (MRSA), has increased at an alarming rate.

It has been reported that more than 50% of all nosocomial infections can be directly related to the transmission of harmful bacteria by healthcare workers who have not properly washed their hands before and after each patient contact. Thus, the best means to prevent transfer of these organisms from patient to patient and to reduce the emergence of resistant organisms is hand-washing with soap and water between patient contacts. The Centers for Disease Control and Prevention (CDC) as well as other regulatory agencies recommend hand-washing before and after each patient encounter. Unfortunately, reports indicate that healthcare workers adhere to hand-washing guidelines less than 70% of the time. Numerous strategies have been attempted to increase healthcare worker compliance to hand-washing, but all have been largely unsuccessful.

There are many possible reasons for non-compliance with recommended hand-washing practices. For example, there may not be sufficient time to properly wash hands or wash stations may be placed in inconvenient locations. Some people simply forget to wash their hands. Others may not realize how infrequently or inadequately they comply with recommended hand-washing practices. Others still may not fully understand the benefits of hand-washing. Some or all of these issues may be addressed if means were provided to monitor compliance with recommended hand-washing practices.

The problem of insufficient hand-washing is becoming worse. Hospitals, through staff reductions, are requiring healthcare workers to attend to more patients during the healthcare provider's work shift. Additionally, high transmission rates of antibiotic resistant bacteria and viruses require greater adherence to the CDC hand-washing guidelines. Hospital administrations are searching for products and services that encourage hand-washing, and a means to ensure and measure compliance.

Similar concerns exist in other industries, such as those relating to the processing and preparation of food. The U.S. Food and Drug Administration's Food Code (the "Food Code") provides guidelines for preparing food and preventing food-borne illness. Retail outlets such as restaurants and grocery stores and other institutions such as nursing homes are subject to the Food Code. In addition to requiring employees to wash their hands, the Food Code requires their employer to monitor the employees' hand-washing. Despite such extensive efforts to ensure that proper hand-washing is performed, more than a quarter of all food-borne illnesses (estimated that food-borne diseases cause approximately 76 million illnesses, 325,000 hospitalizations, and 5,000 deaths in the United States each year) are thought to be due to improper hand-washing.

Numerous prior developments have been advanced as a solution to inadequate hand-washing compliance. One prior development was directed to touch-free and automatic soap: dispensers, faucets, and hand dryers. This prior development was an attempt to make it easier for employees to wash and sanitize their hands. This prior development, however; failed to ensure that the employees actually washed or that the wash was adequate or followed best practices.

Another prior development was directed to alerting someone of the need to wash their hands. This prior development implemented a reporting system worn by a worker, which was activated when the worker leaves a specific area. The reporting system was deactivated when brought near a hand cleaning station, and then only when it was determined that the worker has used the hand cleaning station. This prior development improved the ability to ensure a hand-wash was done but did not ensure that a hand-wash compliant to standards was performed.

Solutions have been long sought but all prior developments have not taught or suggested any complete solutions, and solutions to these problems have long eluded those skilled in the art. Thus there remains a considerable need for devices and methods that can ensure a hand-wash complies with a prescribed government or industry-approved regimen.

SUMMARY

A compliance system and methods, providing the ability to detect and incentivize compliant sanitization and washing procedures are disclosed. The compliance system and methods can include: sensing a user's hand-wash motions; estimating hand-wash scrubs per minute based on the user's hand-wash motions; counting a total hand-wash scrubs based on the user's hand-wash motions; estimating hand-wash vigor based on the user's hand-wash motions; calculating a hand-wash score based on the hand-wash vigor; displaying the hand-wash vigor, the total hand-wash scrubs, and the hand-wash scrubs per minute on a display; and displaying a timer that counts down based on the hand-wash vigor.

Other contemplated embodiments can include objects, features, aspects, and advantages in addition to or in place of those mentioned above. These objects, features, aspects, and advantages of the embodiments will become more apparent from the following detailed description, along with the accompanying drawings.

BRIEF DESCRIPTION OF THE DRAWINGS

The compliance system is illustrated in the figures of the accompanying drawings which are meant to be exemplary

DETAILED DESCRIPTION

Figure 1:
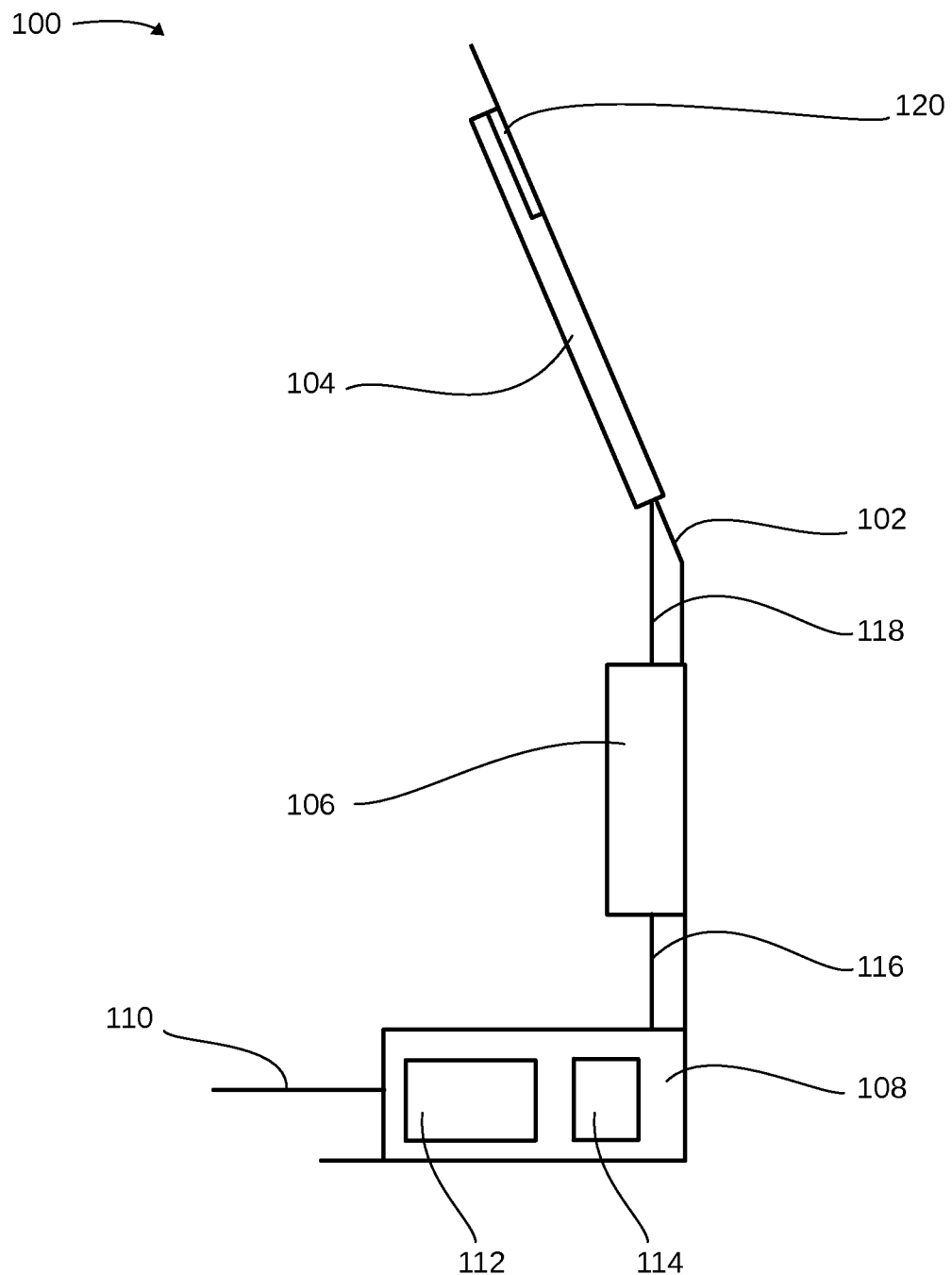
FIG. 1 is a side view of the compliance system.

In the following description, reference is made to the accompanying drawings that form a part hereof, and in which are shown by way of illustration, embodiments in which the compliance system may be practiced. It is to be understood that other embodiments may be utilized and structural changes may be made without departing from the scope of the compliance system.

When features, aspects, or embodiments of the compliance system are described in terms of steps of a process, an operation, a control flow, or a flow chart, it is to be understood that the steps can be combined, performed in a different order, deleted, or include additional steps without departing from the compliance system as described herein.

The compliance system is described in sufficient detail to enable those skilled in the art to make and use the compliance system and provide numerous specific details to give a thorough understanding of the compliance system; however, it will be apparent that the compliance system may be practiced without these specific details.

In order to avoid obscuring the compliance system, some well-known system configurations are not disclosed in detail. Likewise, the drawings showing embodiments of the system are semi-diagrammatic and not to scale and, particularly, some of the dimensions are for the clarity of presentation and are shown greatly exaggerated in the drawing FIGs.

As used herein, the term system is defined as a device or method depending on the context in which it is used. For expository purposes, the term "horizontal" as used herein is defined as a plane parallel to the top plane or surface of the housing, regardless of its orientation. The term "vertical" refers to a direction perpendicular to the horizontal as just defined. Terms, such as "above", "below", "bottom", "top", "side", "higher", "lower", "upper", "over", and "under", are defined with respect to the horizontal plane.

Referring now to FIG. 1, therein is shown a side view of the compliance system 100. The compliance system 100 is shown having a chassis 102 supporting user interface 104, sensors 106, and a power unit 108.

The power unit 108 can include electric converters 112 such as transformers, or AC to DC converters. The power unit 108 can be plugged into an external power source (not shown) with a power cable 110.

Power can be provided via the power cable 110 to the power unit 108 either as DC power or AC. If it arrives to the power unit 108 as AC it is converted in the power unit 108. In one contemplated embodiment, the power unit 108 includes batteries 114 that charge when the power unit 108 is plugged into a DC outlet or an AC outlet.

It is contemplated that the compliance system 100 may be placed next to a sink to wirelessly operate from the batteries' 114 power or plugged in with the power cable 110 to operate without the need to recharge and without the expense of outfitting the power unit 108 with the batteries 114. DC power can travel from the power unit 108 to the sensors 106 via an internal power conduit 116.

The sensors 106 can be image or light sensitive sensors, such as infrared cameras or video cameras. The sensors 106 can have sampling frequencies for sensing the frequencies produced by a user scrubbing his hands. For example, the Nyquist frequency (half the frequency of the data sampling frequency) can be above a likely frequency of scrubbing of a compliant hand-wash.

One contemplated embodiment of the compliance system 100 can implement the sensors 106 as a thermal imaging device dependent on long-wave infrared sensing and capable of operating at room temperature without special cooling. For example, the sensors 106 implemented as an Infra Red (IR) camera as just described could collect a grid of 100×100 pixels at a frequency of 9 hertz (Hz). It is contemplated that this embodiment could implement a Nyquist frequency of 4.5 Hz, which results in the data sampling frequency of 9 Hz.

A further contemplated embodiment of the compliance system 100 can implement the sensors 106 as a color video camera, which as an illustrative example could operate at a resolution operating at resolution of 1024×768 and a frame rate of 30 Hz. It is contemplated that this embodiment could implement a Nyquist frequency of 15 Hz, which results in the data sampling frequency of 30 Hz.

A further contemplated embodiment of the compliance system 100 can implement the sensors 106 as a sound volume sensor collecting the average volume of sound over 50 milliseconds at a rate of 20 Hz. Such a sensor may be tuned to only sense the volume of audio sound at a certain frequency such as a kilohertz.

It has been discovered that having the sensors 106 implemented as an IR camera having a Nyquist frequency of 4.5 Hz and a data sampling frequency of 9 Hz or the sensors 106 implemented as a video camera having a sampling frequency of 30 Hz and the Nyquist frequency of 15 Hz provides the unexpected benefit of reducing manufacturing costs while simultaneously excluding false positive signals when detecting vigor and scrubs from a user engaging the compliance system 100.

It has been discovered that the sensors 106 can provide beneficial results when the sensors' 106 sampling frequency is at least four times the likely scrub frequency. This sample rate has been discovered to enable the compliance system 100 to capture and identify a symmetrical scrubbing motion whose data may appear during analysis to be twice the actual repetition rate of the scrub.

Illustratively, it can be difficult to detect an apex or midpoint of a perpendicular (back and forth) scrub. That is, it is difficult to detect, for example, when a left hand extended fully forward and a right hand retracted fully backward during the scrubbing motion. The midpoint would be where the hands are aligned. It has been discovered that using a sampling rate with the Nyquist frequency at least double the scrub repetition frequency can accurately detect these scrubbing motions.

The sensors 106 can be coupled to the user interface 104 with an internal communication conduit 118 and can deliver the pixel information to the user interface 104. The user interface 104 is contemplated to be a display screen, an interactive display screen, speakers, or a combination thereof.

The sensors 106 can detect when a user is within range of the sink. When the sensors 106 detect the user within range of the sink a game can be activated if the sensors 106 also detect the user is scrubbing or washing their hands.

The game can be displayed on the user interface 104 and can provide the user with feedback on the vigor and duration of their scrubbing or washing. The user interface 104 can further provide feedback to the user regarding whether or not the user is complying with hand-washing standards or best practices.

The user interface 104 is shown having a processor 120. The processor 120 may be integrated into the user interface 104, the sensors 106, or a combination thereof. In the case that the processor 120 is integrated into the sensors 106 then the output of the processor 120 can be sent to the user interface 104 over the internal communication conduit 118.

It is further contemplated that the processor 120 can exist independently and be mounted independently on the chassis 102. The processor 120 can process the pixel information, perform analysis, and update the user interface 104 to advise or signal the user.

Figure 2:
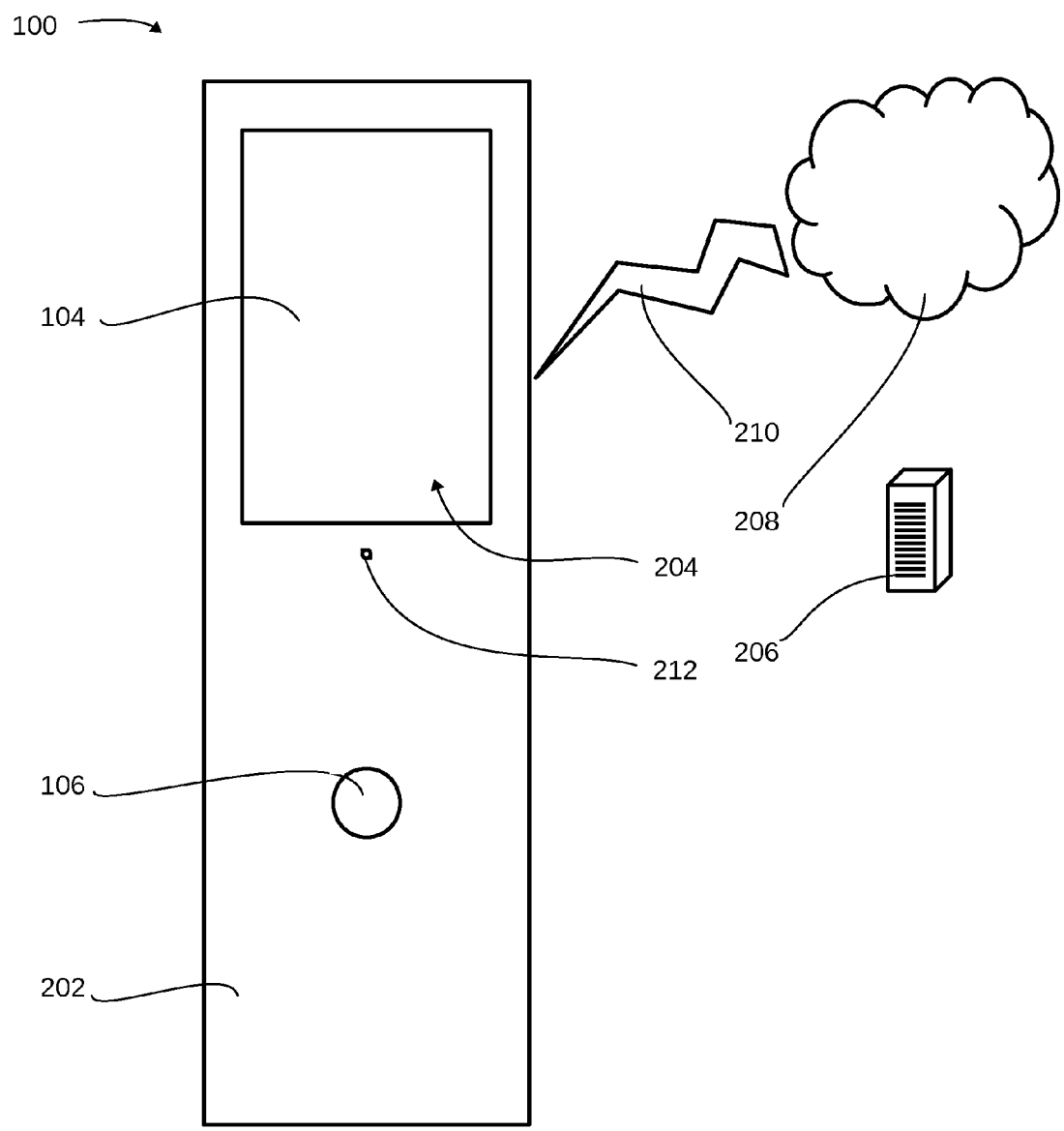
FIG. 2 is a front view of the compliance system of FIG. 1.

Referring now to FIG. 2, therein is shown a front view of the compliance system 100 of FIG. 1. The compliance system 100 is shown having the user interface 104 and the sensors 106 partially enclosed within a housing 202.

The housing 202 can be mounted to the chassis 102 of FIG. 1 and can fully encapsulate the power unit 108 of FIG. 1. It is contemplated that user interface 104, and the sensors 106 can be partially exposed from the housing 202 in order to allow for resistance to splashing liquid.

The housing 202 is contemplated to be implemented with antimicrobial plastic using antimicrobial sealant to create a watertight fixture. The housing 202 can further include a cover 204 over the sensor 106.

The cover 204 can be transparent to wavelength of light that is being sensed by the sensors 106. The cover 204 may enable the sensors 106 to remain within the housing 202 without any physical external exposure.

In one contemplated embodiment the cover 204 can be a layer of ethylene, such as a 1/32 inch plastic piece form fitted and sealed to the housing 202. The housing 202 can provide a water tight seal that allows the compliance system 100 to be scrubbed with cleaners and abrasives for maintaining a sanitary condition.

It is further contemplated that the housing 202 can provide a watertight seal for the connection between the power cable 110 of FIG. 1 and the power unit 108 of FIG. 1. It is yet further contemplated that the housing 202 can provide a watertight environment within the housing 202 when the power cable 110 is disconnected and the power unit 108 is running off of the batteries 114 of FIG. 1.

The processor 120 of FIG. 1 is contemplated to keep a log of its operation in a local database 206 having non-transitory computer readable medium or in a remote database 208 having non-transitory computer readable medium, and to which the processor 120 may connect via radio 210 such as WiFi or cellular. As an illustrative example, the user interface 104 can be a smartphone that connects to a hospital's WiFi network or to the Internet via cellular radio transmission.

It is contemplated that the compliance system 100 can further include low power sensors 212 exposed from the housing 202 on the compliance system 100. The low power sensors 212 can be used to detect whether any users are within an observation area. The low power sensors 212 can be motion sensors with a Fresnel lens and a pair of comparator-based single-pixel thermal sensors, commonly referred to as a passive infrared sensor, or "PIR".

Figure 3:
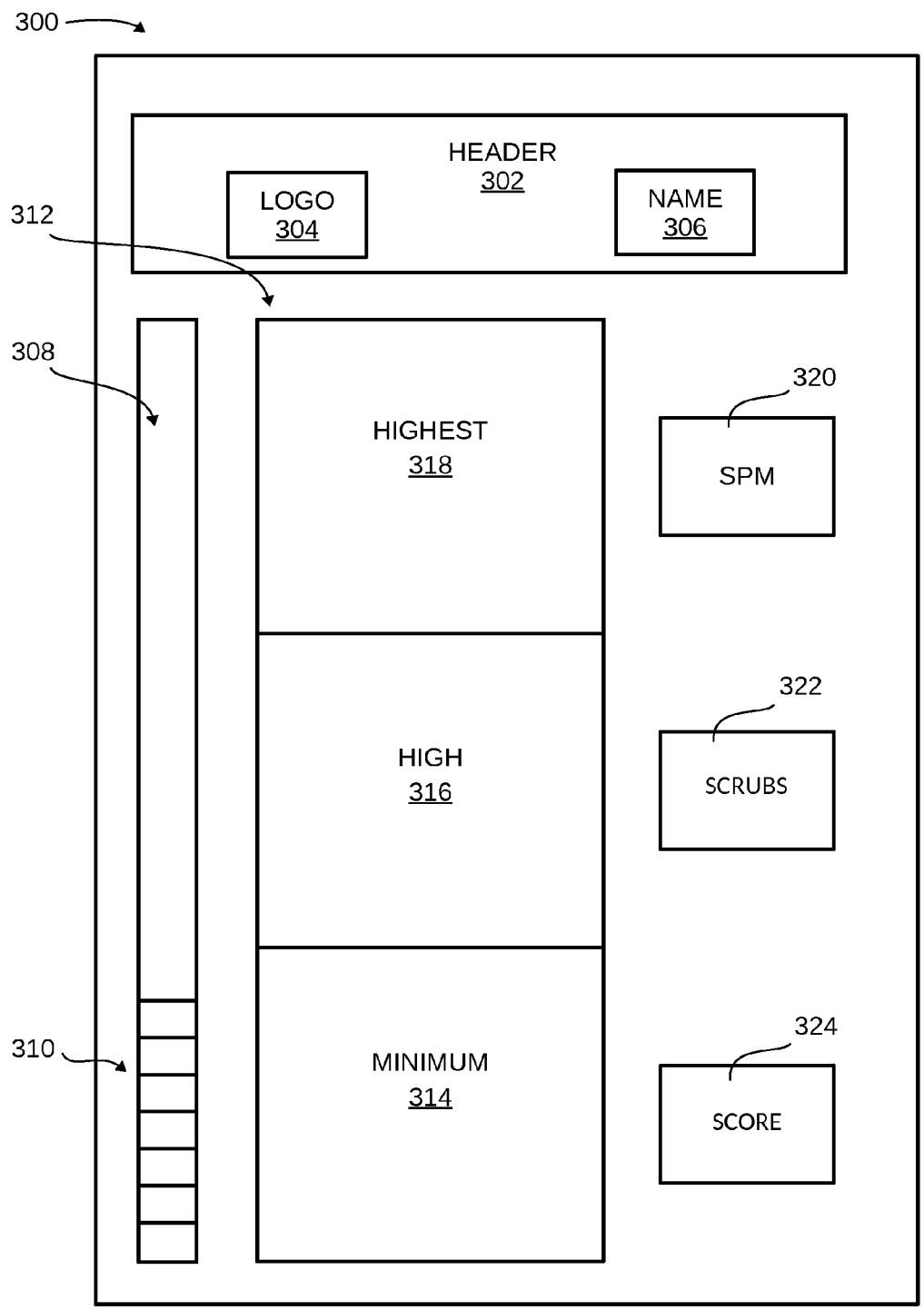
FIG. 3 is a graphical view of a main screen display for the compliance system of FIG. 1.

Referring now to FIG. 3, therein is shown a graphical view of a main screen display 300 for the compliance system 100 of FIG. 1. The main screen display 300 may be shown or displayed on the user interface 104 of FIG. 1. The main screen display 300 can inform the user about the analysis being conducted by the processor 120 of FIG. 1 on their hand-washing actions detected by the sensors 106 of FIG. 1.

The main screen display 300 can include a header 302 that includes a logo 304 and a name 306. Below the header 302 is a time meter 308 having individual time meter levels 310. The individual time meter levels 310 can climb or be added cumulatively from one endpoint of the meter to the other endpoint. For example, the individual time meter levels 310 could be added each second a satisfactory or compliant hand-wash is sensed. The individual time meter levels 310 could be added to the time meter 308 starting at the bottom and progressing to the top after the allotted time for a satisfactory or compliant hand-wash had elapsed.

It is contemplated that the time meter 308 can correspond to a particular color indicating the amount of time that remains to be analyzed in order for the compliance system 100 to register a user's hand-wash as compliant or satisfactory. For example, if the compliance system 100 is configured to require the detection of a 30 second hand-wash then the time meter 308 might be completely lit blue at the start of the wash and transition to a different color as the hand-wash approaches the 30 second time threshold.

It is further contemplated that the individual time meter levels 310 can correspond to a particular color indicating the amount of time that remains to be analyzed in order for the compliance system 100 to register a user's hand-wash as compliant or satisfactory. For example, if the compliance system 100 is configured to require the detection of a 30 second hand-wash then the time meter 308 could include 30 individual time meter levels 310 that change color of each successively higher individual time meter levels 310 each second a satisfactory or compliant hand-wash is detected.

Adjacent to the time meter 308 is a vigor meter 312. The vigor meter 312 can include a minimum compliance indicator 314, a high compliance indicator 316, and a highest compliance indicator 318.

The vigor meter 312 may indicate the current level of vigor that is perceived by the sensors 106 and the analysis of the information generated by the sensors 106. The vigor meter 312 can provide feedback to users enabling the users to increase their vigor if they are moving too slowly. The vigor meter 312 can also require a continuous presence and motion from the user, thereby potentially preventing an unconscious rationalization that might prevent a compliance wash.

When only the minimum compliance indicator 314 is lit, this can signal the user that a minimum level of vigor is being recognized by the compliance system 100. When the minimum compliance indicator 314 and the high compliance indicator 316 are lit, this can signal the user that a high level of vigor is being recognized by the compliance system 100. When the minimum compliance indicator 314, the high compliance indicator 316, and the highest compliance indicator 318 are lit, this can signal the user that the highest level of vigor is being recognized by compliance system 100.

It is contemplated that the minimum compliance indicator 314 can be red and can indicate a hand-wash with a low vigor reading and that the current level of the user's hand-wash vigor would reduce the user's score in a hand-wash vigor game. It is contemplated that the high compliance indicator 316 can be yellow and can indicate a hand-wash with an adequate vigor reading and that the current level of the user's hand-wash vigor would slowly increase the user's score in the hand-wash vigor game.

It is contemplated that the highest compliance indicator 318 can indicate a hand-wash with a highly compliant vigor reading and that the current level of the user's vigor would quickly increase the user's score in the hand-wash game and could result in a high score. Adjacent to the vigor meter 312 is a scrubs per-minute meter 320, a total scrubs meter 322, and a score meter 324.

The scrubs per-minute meter 320 can indicate the scrubs-per-minute (SPM) estimated to be performed if the user's scrubbing continues as it has been for a full minute. As an example, a value of 60 could indicate that 60 SPM are estimated to be performed if the current scrubbing continues for a full minute.

The compliance system 100 can include a threshold that could identify a low SPM. It is contemplated that 60 SPM may be indicative a low SPM. An SPM below the threshold could be used to indicate to the user that an inadequate level of vigor is being used in the current scrubbing motion.

The total scrubs meter 322 can indicate to the user the total number of scrubs that have been recognized by the compliance system 100, which may imbue a sense of accomplishment and encouragement when paired with the individual time meter levels 310 remaining on the time meter 308 slowly changing color downward toward an indication of completion.

For example, displaying "55" in the total scrubs meter 322 might be used to indicate to the user that 55 scrubs have been performed. The score meter 324 can be another means of communicating to the user the amount of vigorous scrubbing they have performed. In one contemplated embodiment the score meter 324 calculates a score as a multiple of Total Scrubs. In another contemplated embodiment the score meter 324 calculates a score that increases exponentially so that the rate of score increase increases as the wash continues to progress.

Figure 4:
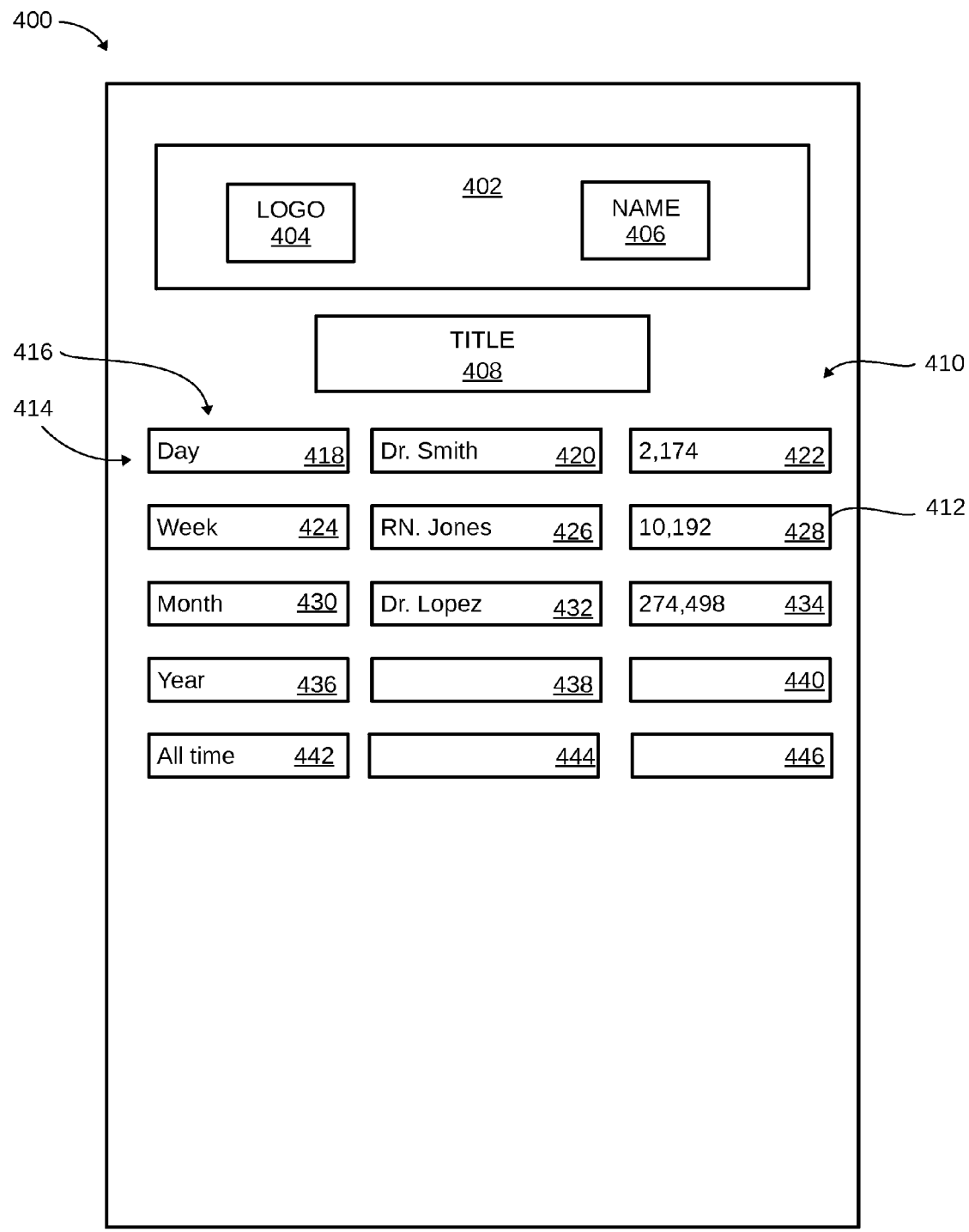
FIG. 4 is a graphical view of a high score screen display for the compliance system of FIG. 1.

Referring now to FIG. 4, therein is shown a graphical view of a high score screen display 400 for the compliance system 100 of FIG. 1. The high score screen display 400 can be displayed on the user interface 104 of FIG. 1.

The high score screen display 400 can include a header 402 that includes a logo 404 and a name 406. Below the header 402 a title 408 is shown. As an illustrative example the title 408 can be "High Scores".

Below the header 402 and the title 408 is a score board 410 having cells 412 arranged in rows 414 and columns 416. The rows 414 can be seen arranged in five rows and the columns 416 can be arranged in three columns.

The row 414 in the top position of the score board 410 can include a day cell 418 indicating that the data in the first row corresponds to data for a day, a day name cell 420 providing the name of the holder of the high score for the current day, and a day score cell 422 providing the record holding score for the current day.

The row 414 in the second position from the top of the score board 410 can include a week cell 424 indicating that the data in the second row corresponds to data for a week, a week name cell 426 providing the name of the holder of the high score for the current week, and a week score cell 428 providing the record holding score for the current week.

The row 414 in the third position from the top of the score board 410 can include a month cell 430 indicating that the data in the third row corresponds to data for a month, a month name cell 432 providing the name of the holder of the high score for the current month, and a month score cell 434 providing the record holding score for the current month.

The row 414 in the fourth position from the top of the score board 410 can include a year cell 436 indicating that the data in the fourth row corresponds to data for a year, a year name cell 438 providing the name of the holder of the high score for the current year, and a year score cell 440 providing the record holding score for the current year.

The row 414 in the fifth position from the top of the score board 410 can include an all time cell 442 indicating that the data in the fifth row corresponds to data for all time, an all time name cell 444 providing the name of the holder of the current high score, and an all time score cell 446 providing the record holding score.

It is contemplated that when one of the rows 414 corresponds to a time span that has not yet passed, the rows 414 following thereafter, which are for longer time spans, might not list a name or high score since it would be identical to the name and high score above it. As an illustrative example, the score board 410 is shown having the year name cell 438, the year score cell 440, the all time name cell 444, and the all time score cell 446 empty to indicate a year has not passed since the compliance system 100 has collected data.

Figure 5:
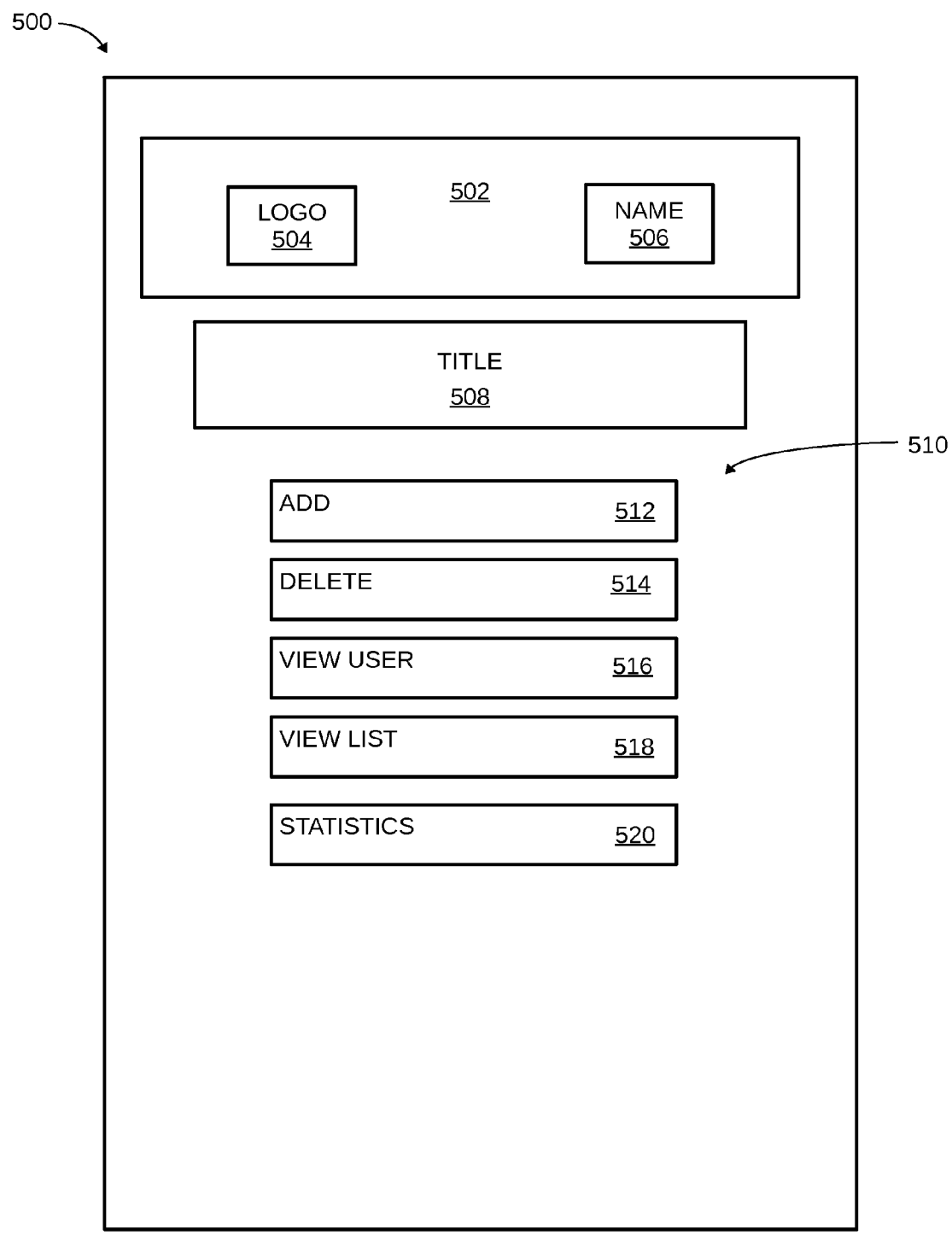
FIG. 5 is a graphical view of an administrator screen display for the compliance system of FIG. 1.

Referring now to FIG. 5, therein is shown a graphical view of an administrator screen display 500 for the compliance system 100 of FIG. 1. The administrator screen display 500 can be displayed on the user interface 104 of FIG. 1. The administrator screen display 500 can provide an interface with the local database 206 of FIG. 2 or the remote database 208 of FIG. 2 that store activity records for the compliance system 100.

It is contemplated that the administrator screen display 500 can be used or displayed on a cellular phone or on a web page. The administrator screen display 500 can include a header 502 that includes a logo 504 and a name 506. Below the header 502 a title 508 is shown. The title 508 shown on the administrator screen display 500 can be "Administrator Monitor".

The administrator screen display 500 can include buttons 510 below the title 508. It is contemplated that the buttons 510 can enable an Administrator to perform a review or to make changes to the compliance system 100.

The button 510 at the top just below the title 508 is an add user button 512. The add user button 512 enables an administrator to add a new user, such as a new employee of a hospital in which the compliance system 100 operates. The add user button 512 may bring up a text box that enables entry of the new user's name. Typing the enter key may complete the add user action and update the local database 206 or the remote database 208 holding the user's information.

The button 510 below the add user button 512 is a delete user button 514. The delete user button 514 can cause the compliance system 100 to display the user's list screen display 700 of FIG. 7, and allow the administrator to select a user and delete them using the select button 734 of FIG. 7.

The button 510 below the delete user button 514 is a view user button 516. The view user button 516 prompts the compliance system 100 to display the view user screen display 600 of FIG. 6.

The button 510 below the view user button 516 is a view user list button 518. The view user list button 518 can cause the compliance system 100 to display the user's list screen display 700 of FIG. 7.

The button 510 below the view user list button 518 is a statistics button 520. The statistics button 520 can cause the compliance system 100 to display the statistics screen display 800 of FIG. 8.

Figure 6:
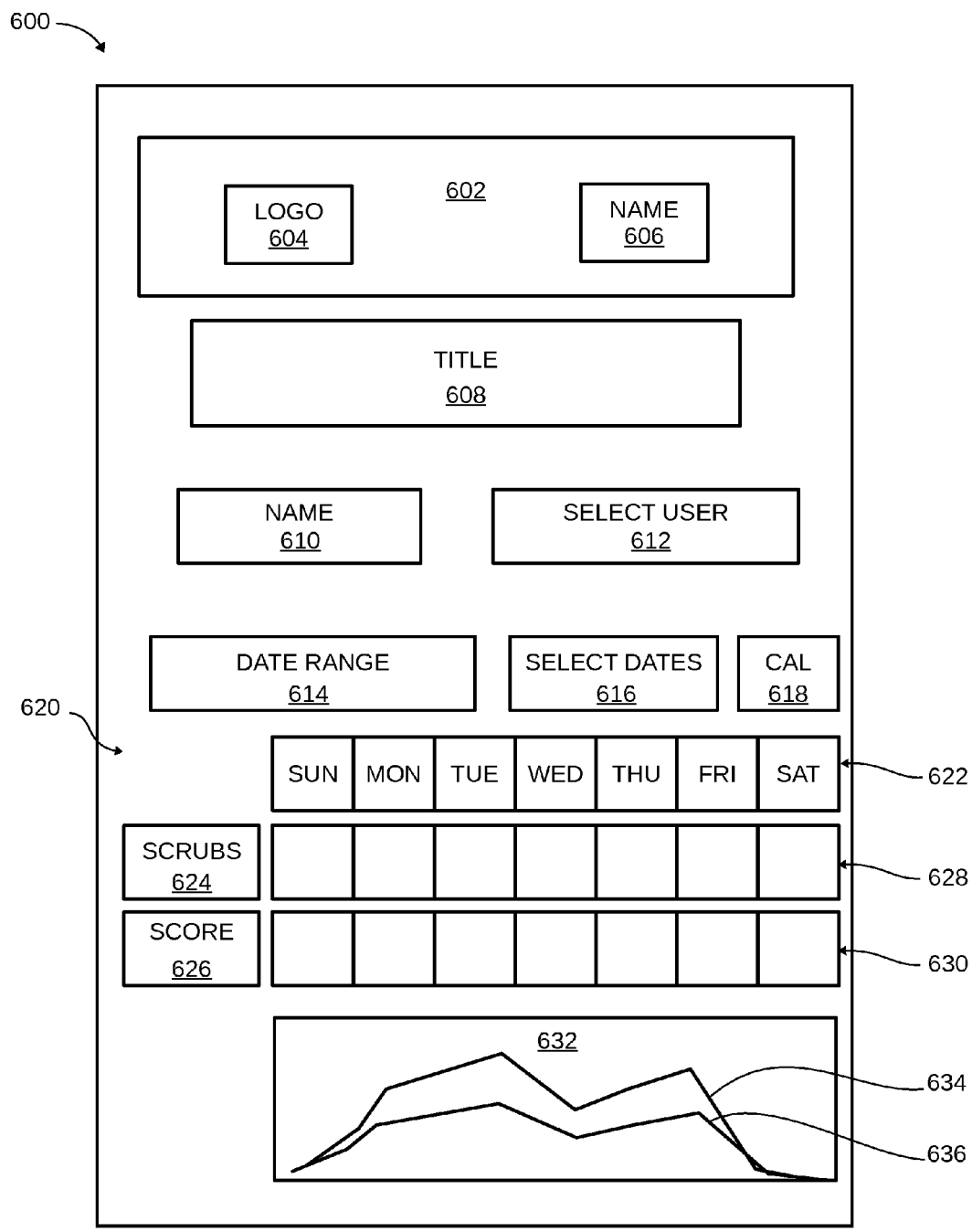
FIG. 6 is a graphical view of a view user screen display for the compliance system of FIG. 1.

Referring now to FIG. 6, therein is shown a graphical view of a view user screen display 600 for the compliance system 100 of FIG. 1. The view user screen display 600 can be displayed on the user interface 104 of FIG. 1. It is contemplated that the view user screen display 600 can be displayed by the compliance system 100 when an administrator clicks the view user button 516 of FIG. 5 and then selects a user on the user's list screen display 700 of FIG. 7.

The view user screen display 600 can include a header 602 that includes a logo 604 and a name 606. It is contemplated that the logo 604 can be an active button that will prompt the compliance system 100 to take the administrator back to the administrator screen display 500 of FIG. 5 when engaged. Below the header 602 a title 608 is shown. The title 608 shown on the view user screen display 600 can be "View User".

Below the title 608 a name cell 610 can be displayed and can contain a user's name corresponding to the profile that is being displayed by the view user screen display 600. Adjacent to the name cell 610 and below the title 608 is a select user button 612.

The select user button 612 can be used to enable an administrator to select a different user from the user's list screen display 700. When a different user is selected from the user's list screen display 700, view user screen display 600 would be refreshed and repopulated with the newly selected user's information.

Below the name cell 610 is a date label 614. The date label 614 can display a week within which vigor and scrub data for the user is shown. Adjacent to the date label 614 and below the select user button 612 is a select dates button 616.

The select dates button 616 can be engaged after a week has been selected from a calendar display 618. Once the week from the calendar display 618 is selected and the select dates button 616 is engaged, the data corresponding to the selected weeks will be displayed in a user data chart 620 for the user.

The user data chart 620 can be positioned below the select dates button 616 and below the date label 614. The user data chart 620 can include a top row of day labels 622 that list the days of a week from Sunday through Saturday.

The user data chart 620 can further include a scrubs count label 624 and a score label 626. The scrubs count label 624 can correspond to scrubs data cells 628. The scrubs data cells 628 can display the total scrubs detected by the compliance system 100 for each day indicated by the day labels 622.

The score label 626 can correspond to score data cells 630. The score data cells 630 can display the total score calculated by the compliance system 100 for each day indicated by the day labels 622. Below the user data chart 620 a user data graph 632 is shown graphically depicting the user's scrubs 634 from the scrubs data cells 628, the user's score 636 from the score data cells 630, or a combination thereof.

Figure 7:
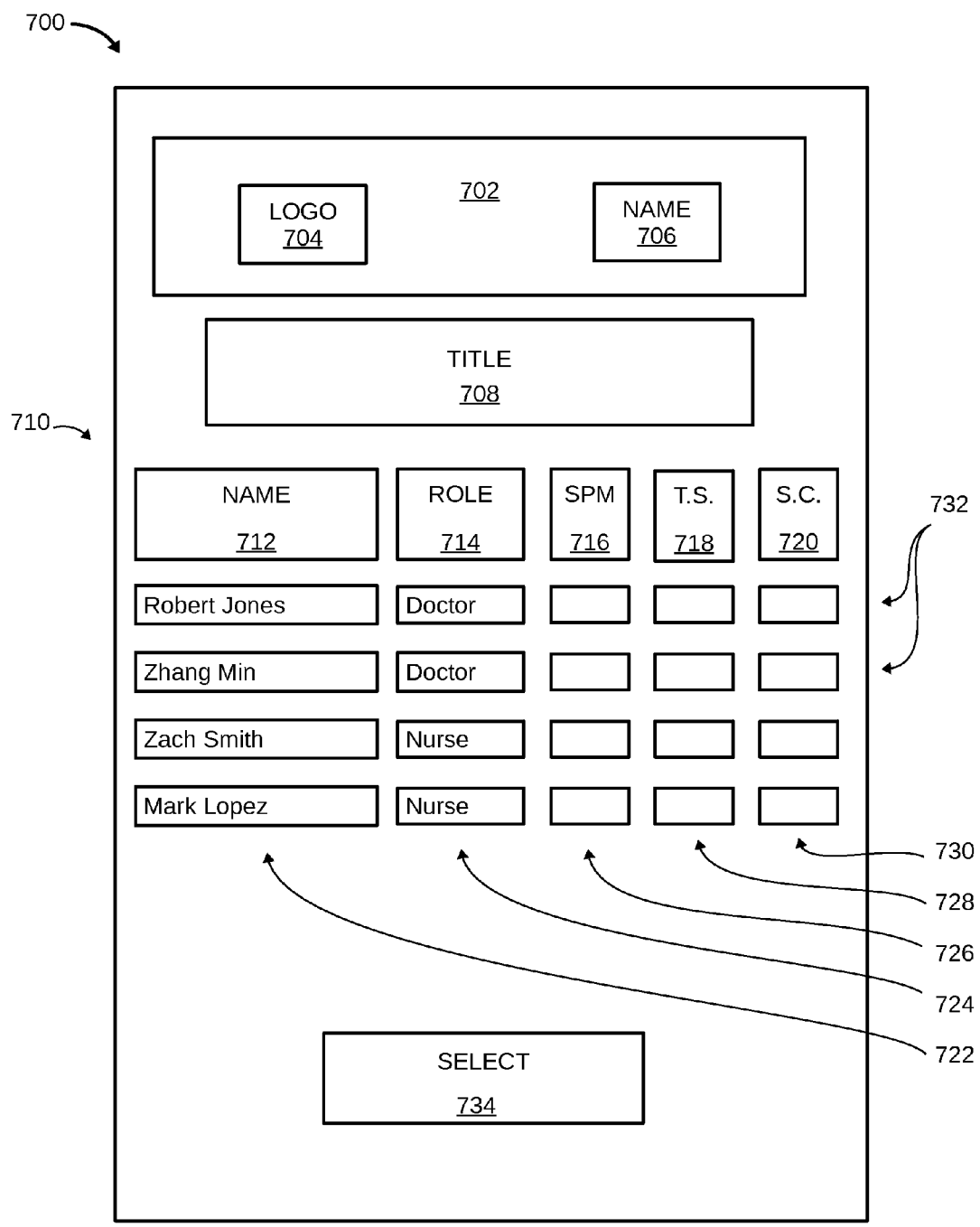
FIG. 7 is a graphical view of a user's list screen display for the compliance system of FIG. 1.

Referring now to FIG. 7, therein is shown a graphical view of a user's list screen display 700 for the compliance system 100 of FIG. 1. The user's list screen display 700 can be displayed on the user interface 104 of FIG. 1.

The user's list screen display 700 can include a header 702 that includes a logo 704 and a name 706. It is contemplated that the logo 704 can be an active button that will prompt the compliance system 100 to take the administrator back to the administrator screen display 500 of FIG. 5 when engaged. Below the header 702 a title 708 is shown. The title 708 shown on the user's list screen display 700 can be "List of Users".

Below the title 708 the user's list screen display 700 can include a user list 710. The user list 710 can include a name label 712, a role label 714, an SPM label 716, a total scrubs label 718, and a score label 720.

The name label 712 can correspond to name fields 722. The role label 714 can correspond to role fields 724. The SPM label 716 can correspond to SPM fields 726. The total scrubs label 718 can correspond to total scrub fields 728. The score label 720 can correspond to score fields 730.

The user list 710 includes the name fields 722, the role fields 724, the SPM fields 726, the total scrub fields 728, and the score fields 730 in rows that each correspond to a user 732. Each of the users 732 can have data occupying a single row. It has been discovered that displaying the users 732 in rows enables an administrator to quickly assess the information and to see overall or recent statistics of all the users on one screen.

Below the user list 710 a select button 734 is depicted near the bottom of the user's list screen display 700. The select button 734 is contemplated to be a multifunction button based on how the administrator arrived at the user's list screen display 700.

It is contemplated that the user's list screen display 700 can be displayed by the compliance system 100 when an administrator clicks the select user button 612 of FIG. 6. When the administrator selects the user 732 and engages the select button 734 the compliance system 100 will display the view user screen display 600 of FIG. 6.

It is contemplated that the user's list screen display 700 can be displayed by the compliance system 100 when an administrator clicks the view user button 516 of FIG. 5. When the administrator selects the user 732 and engages the select button 734 the compliance system 100 will display the view user screen display 600.

It is contemplated that the user's list screen display 700 can be displayed by the compliance system 100 when an administrator clicks the delete user button 514 of FIG. 5. When the administrator selects the user 732 and engages the select button 734 the compliance system 100 can remove the user 732 that the administrator selected from the user list 710. The compliance system 100 can also remove any of the information for the user 732 that was selected from the local database 206 of FIG. 2 or the remote database 208 of FIG. 2, and the compliance system 100 can then display the administrator screen display 500.

It is contemplated that the user's list screen display 700 can be displayed by the compliance system 100 when an administrator clicks the view user list button 518 of FIG. 5. It is contemplated that when the user's list screen display 700 is displayed in response to an engagement of the view user list button 518, the select button 734 may not appear to the administrator. Alternatively it is contemplated that when the user's list screen display 700 is displayed in response to an engagement of the view user list button 518, the select button 734 may be visible and when engaged would prompt the compliance system 100 to display the administrator screen display 500.

Figure 8:
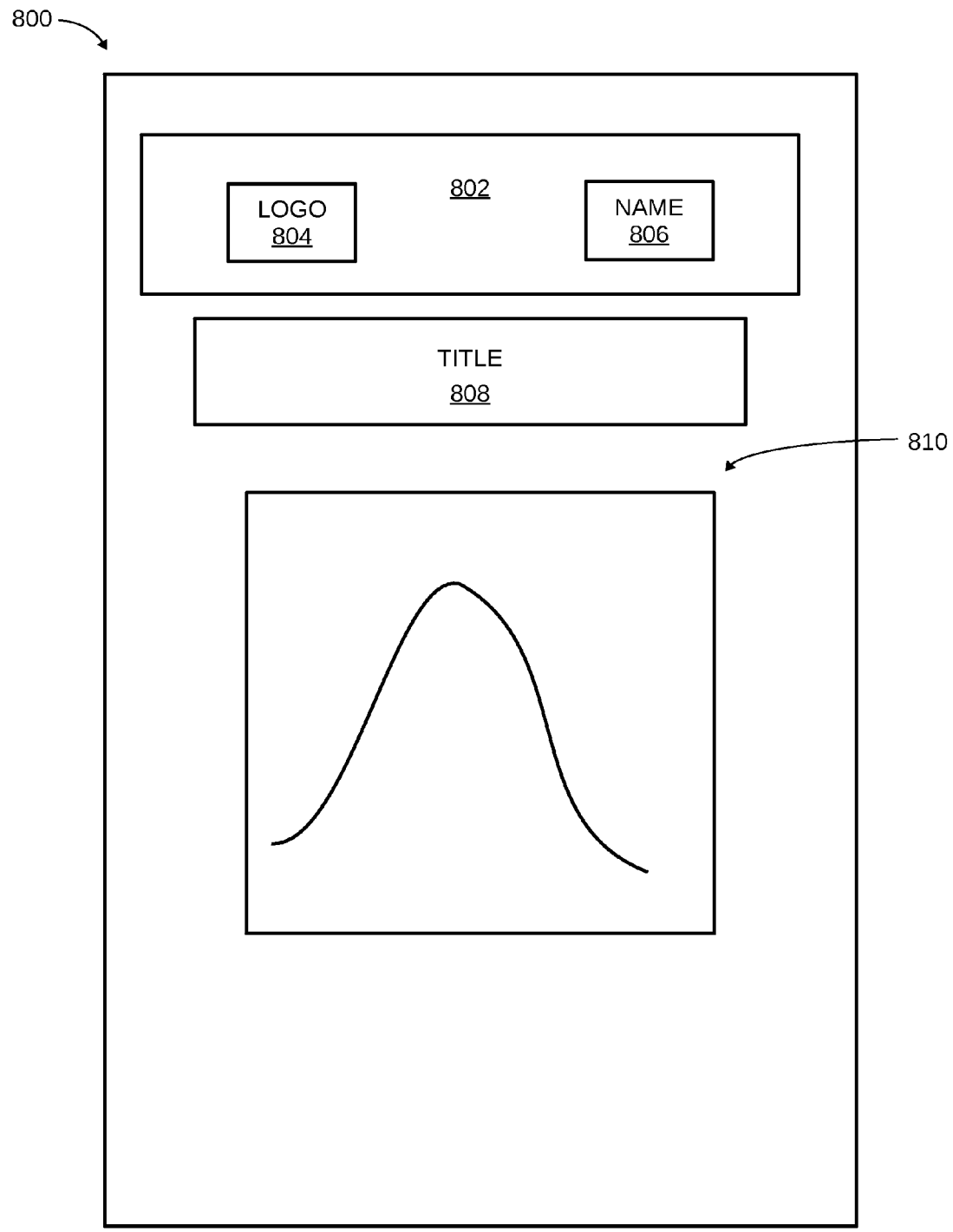
FIG. 8 is a graphical view of a statistics screen display for the compliance system of FIG. 1.

Referring now to FIG. 8, therein is shown a graphical view of a statistics screen display 800 for the compliance system 100 of FIG. 1. The statistics screen display 800 can be displayed on the user interface 104 of FIG. 1.

The statistics screen display 800 can include a header 802 that includes a logo 804 and a name 806. Below the header 802 a title 808 is shown. The title 808 shown on the statistics screen display 800 can be "Statistics Monitor".

The statistics screen display 800 can include statistics 810 below the title 808. The statistics 810 can include the number of days the compliance system 100 has been running or the number of hand-washes that sensor analysis has recognized as compliant.

Figure 9:
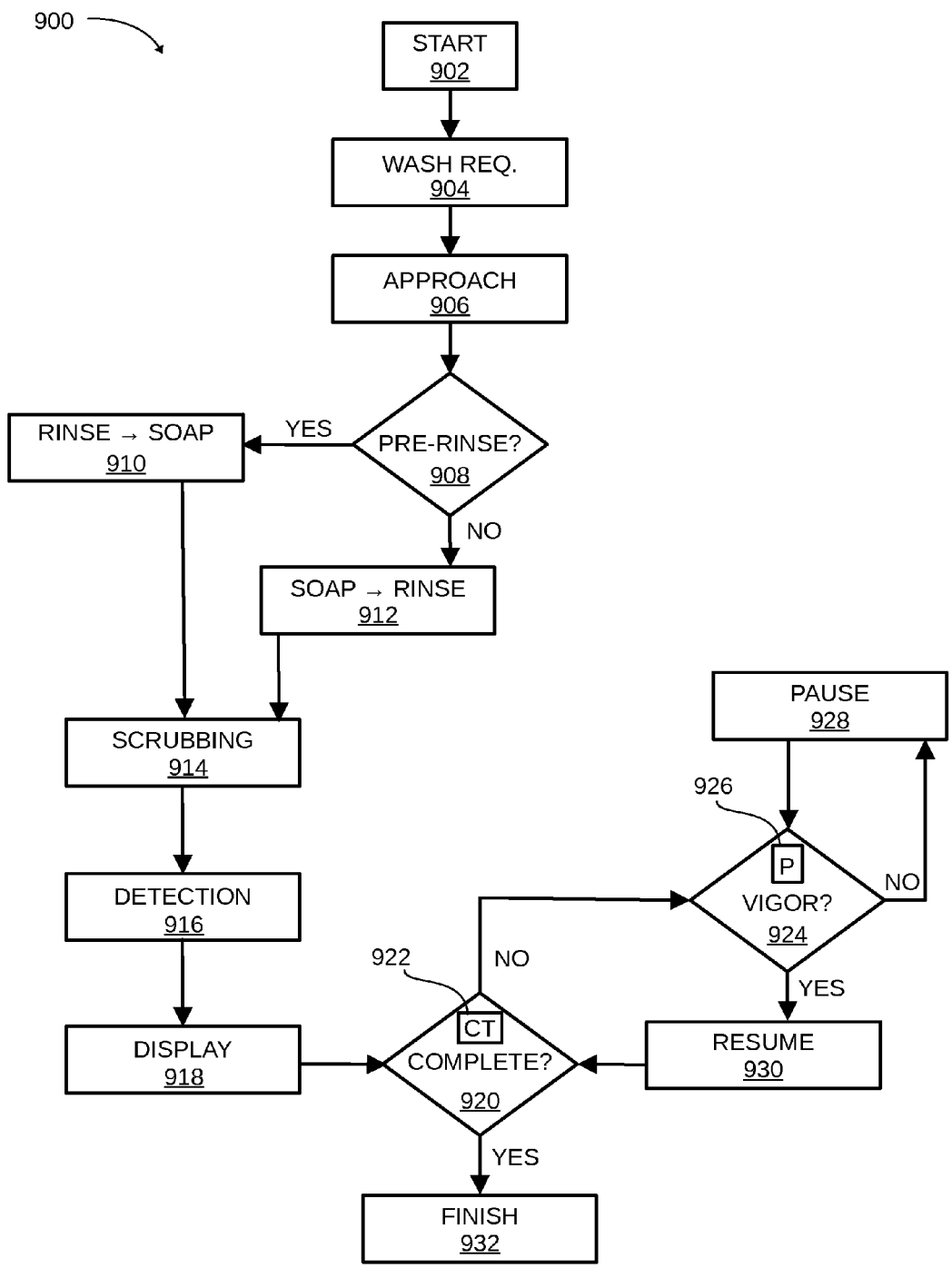
FIG. 9 is a control flow for operating the compliance system of FIG. 1.

Referring now to FIG. 9, therein is shown a control flow 900 for operating the compliance system 100 of FIG. 1. The control flow 900 provides an overview of how an embodiment of the compliance system 100 assists a user in performing a hand-wash that is compliant with a standard regimen in terms of vigor and time. The level of time and vigor can be configurable.

The control flow 900 can begin with a start step 902. The start step 902 indicates the beginning of the control flow 900 and can initiate or direct a user to a wash required step 904. The wash required step 904 can signify that a user has transitioned tasks and must wash hands.

In the wash required step 904 the user could encounters a situation that calls for washing their hands in order to maintain a compliant environment. The situation could include the exposure of the user to an environment requiring management of harmful microbes, for example, at a hospital.

As an illustrative example, the wash required step 904 could be initiated when a nurse transitions from helping a first patient to helping a second patient. In another illustrative example the wash required step 904 could be initiated when a doctor may arrive back from a lunch break and transitions to performing a checkup on a patient. The user can proceed from the wash required step 904 directly to an approach step 906.

During the approach step 906, the user can proceed to a sink with the compliance system 100. The compliance system 100 can provide vigor and scrubbing data, as described above, from the sensors 106 of FIG. 1 for the region in, above, and around the sink where the user is approaching in the approach step 906. The processor 120 of FIG. 1 can then analyze the data provided by the sensors 106 for detecting scrubbing and vigor.

It is contemplated that when the compliance system 100 is incorporated with fixtures like a sink or a scrub station, the sink or scrub station can be called a sink or scrub station with vigor awareness. The approach step 906 can be connected to a pre-rinse decision step 908. The pre-rinse decision step 908 can be a decision step determining whether a user rinses before applying soap in a rinse→soap step 910 or whether a user applies soap before rinsing in a soap→rinse step 912.

When the result of the pre-rinse decision step 908 is "NO" then the user will proceed to the soap→rinse step 912. When the result of the pre-rinse decision step 908 is "YES" the user will proceed to the rinse→soap step 910.

It is contemplated that the user can turn on the faucet and apply the water in the rinse→soap step 910 or during the soap→rinse step 912. The user might or might not turn the faucet off.

It is contemplated that the compliance system 100 can monitor, detect, and store the result of the pre-rinse decision step 908. In one contemplated embodiment the result of the pre-rinse decision step 908 can be a trigger indicating non-compliance or compliance.

The soap→rinse step 912 as well as the rinse→soap step 910 are connected to a scrubbing step 914. The scrubbing step 914 can be connected to a detection step 916.

It is contemplated that the compliance system 100 can begin detecting vigor and scrubs in the detection step 916 once the sensors 106 detect the hands of a user in the sink region. It is further contemplated that the compliance system 100 can begin detecting vigor and scrubs in the detection step 916 when the sensors 106 detect the hands of the user in motion in or above the sink region.

The detection step 916 can be connected to a display step 918. The display step 918 can update the main screen display 300 of FIG. 3 with the data detected in the detection step 916. That is the scrubs per-minute meter 320 of FIG. 3, the total scrubs meter 322 of FIG. 3, and the score meter 324 of FIG. 3 can display information derived from the detection step 916.

The main screen display 300 can also be updated with the detected vigor, and the time remaining in a scrubbing time countdown can be displayed. The level of vigor detected by the sensors 106 in the detection step 916 can be displayed in the vigor meter 312 of FIG. 3.

The time remaining in the scrubbing session can be displayed in the time meter 308 of FIG. 3. The time remaining in the scrubbing session can decrement every second during which vigorous repetitive motion is detected in the detection step 916.

Alternatively, it is contemplated that a row of LEDs could be used to signal a user in much the same way as the time meter 308. It is contemplated that a row of LEDs could proceed from completely unlit, to one LED being lit, to a contiguous group of 2 LEDs being lit including the first LED, and so on until all LEDs in the row are lit, thereby indicating that the compliance system 100 has detected in accordance with its operation that the hand-wash was compliant and is complete.

Once complete, the LEDs may then proceed to flash on and off to provide more visual stimuli to the user that the hand-wash is at least compliant. The estimated SPM calculated by the processor 120 of FIG. 1 based on the timing of the scrubs detected by the sensors 106 in the detection step can be shown in the scrubs per-minute meter 320.

It is contemplated that the compliance system 100 can be implemented without the main screen display 300 but instead could utilize indicators for vigor such as LEDs. As an illustrative example, a set of LEDs including a red LED, yellow LED, and green LED can be used in much the same way as the minimum compliance indicator 314 of FIG. 3, the high compliance indicator 316 of FIG. 3, and the highest compliance indicator 318 of FIG. 3 in the vigor meter 312.

The detection step 916 can trigger the highest compliance indicator 318 when a threshold for frequency is met, such as a threshold of 1 Hz or 1.5 Hz. It is contemplated that the main screen display 300 is activated or remains activated and is updated with values derived from analysis by the processor 120 of the data collected by the sensors 106.

It is contemplated that the values detected or calculated by the compliance system 100 can be uploaded to the local database 206 of FIG. 2 or the remote database 208 of FIG. 2. Logging the detected scrubs per second, the detected vigor, the estimated SPM, and the time remaining in a scrubbing time countdown can enable the administrative audit of the user's performance at a later time.

It is contemplated that the detected scrubs per second, the detected vigor, the estimated SPM, and the time remaining in a scrubbing time countdown can be displayed in a waiting area to patients in order to impress upon the patients that the healthcare establishment in which they find themselves takes the reduction of infection very seriously. The compliance system 100 may further display the detected scrubs per second, the detected vigor, the estimated SPM, and the time remaining in a scrubbing time countdown on web page that is updated online and that users may monitor from their smartphones or computers. It is contemplated that the compliance system 100 may be integrated into the sinks of a restaurant and the statistics collected by the compliance system 100 may be used to update a website in order to impress upon customers the high priority that cleanliness is given at the restaurant establishment.

It is contemplated that the detection step 916 can be triggered by the activation of the water in the sink prompting the compliance system 100 to attempt the detection of scrubbing. In another contemplated embodiment the compliance system 100 is constantly monitoring for scrubbing in the detection step 916 and does not need to detect the user or the activation of the water in the sink before initiating such monitoring in the detection step 916.

The compliance system 100 can be utilized in many ways to ensure a compliant hand-wash was achieved. It is contemplated that in some embodiments the compliance system 100 would not detect the dispensation of soap or the activation of water.

It has been discovered that implementing the compliance system 100 in this low cost embodiment can be more desirable than the added compliance detection that requires the detection of soap dispensation or water activation. This may be the case where the vast majority of noncompliance instances are due to forgetfulness to approach the sink or to continue vigorous scrubbing for a compliant amount of time. In such a case neither the water nor soap dispensing need to be monitored since compliance will only be verified once the scrubbing, an action that succeeds soap and water dispensing, is performed for a sufficient length of time with a sufficient level of vigor.

It is contemplated that the compliance system 100 can use data received from the sensors 106 that detect vigor in the detection step 916 both in the case where the water is left running during the wash in the scrubbing step 914 and in the case that the water is not left running during the scrubbing step 914. It is contemplated that the detection step 916 can include a pre-analysis of the input from the sensors 106 that is designed to detect running water. The compliance system 100 can then choose two different detection methods for the scrubbing and vigor based on whether the pre-analysis detected running water or not.

The display step 918 is connected to a complete decision step 920. The result of the complete decision step 920 is based on a countdown timer 922. The countdown timer 922 is used to determine if the current hand-wash meets the conditions of a compliant hand-wash.

If the countdown timer 922 is found to not have reached zero then the result of the complete decision step 920 is a "NO" and the compliance system 100 can invoke a vigor decision step 924. The vigor decision step 924 can input new sensor data from the sensors 106. The new sensor data can be analyzed in order to detect continued vigor and scrubs.

It is contemplated that the compliance system 100 can include a parameter 926 that increases or decreases the sensitivity of the compliance system 100 to detect vigor. When the parameter 926 is at a high setting the probability of detecting vigor is increased but would also produce more false positives. When the parameter 926 is in a high setting the probability of correctly detecting a lack of vigor is decreased providing fewer true negatives.

Conversely, the parameter 926 can be set low to make detection of vigor and scrubs less probable. It is contemplated that setting the parameter 926 in the high setting may be used in order to decrease the probability of displaying to the user that their hand-wash is noncompliant when the wash is indeed compliant since the vigor detector depends on analysis of the sensors 106 data and is anticipated to occasionally arrive at incorrect conclusions and thus it may be desirable to skew the errors in favor of the user.

It is contemplated that the data captured by the sensors 106 may be collected and processed after the fact in order to determine the typical conditions of detecting a noncompliant hand-wash. If it is found that the vast majority of noncompliance occurs due to premature removal of hands from the sink then the parameter 926 may be set higher because it could be concluded that erroneously detecting hand motion as vigorous hand motion is relatively benign consequence and the incorrect labeling of a compliant hand-wash as noncompliant may have the greater danger of decreasing long term user compliance by decreasing user attention to the vigor-awareness display in the long run.

If vigor is not detected in the vigor decision step 924, the vigor decision step 924 will result in a "NO" and trigger a pause step 928. The pause step 928 can pause the countdown timer 922 and loop back to the vigor decision step 924. The countdown timer 922 may remain paused until vigor is detected again by the vigor decision step 924.

It is contemplated that the vigor decision step 924 can optionally result in the "NO" output when the vigor has not been detected for a preset length of time. It has been discovered that allowing the vigor decision step 924 to result in the "NO" output only after vigor has not been detected for a preset time period favors the likelihood that the user is continuing to scrub and the vigor-detection is merely encountering a glitch of some kind, which could be the obstruction of the sensor or unexpected sensor noise.

Once the vigor decision step 924 detects vigor again, the vigor decision step 924 will result in a "YES" output and the compliance system 100 will invoke a resume step 930. The resume step 930 will continue the countdown of the countdown timer 922.

It is contemplated that the compliance system 100 can optionally track the number of times that the pause step 928 is invoked without returning to the resume step 930. It is contemplated that the compliance system 100 could conclude that the user has stepped away from the sink. In the case where the compliance system 100 concludes the user has stepped away from the sink, the compliance system 100 may reset the countdown timer 922 and return to the detection step 916 for detecting a new user.

If the countdown timer 922 is found to have reached zero then the result of the complete decision step 920 is a "YES" and the compliance system 100 can invoke a finish step 932. The finish step 932 can provide the user an indication that they have successfully completed the monitoring portion of the hand-wash.

It is contemplated that the users may then optionally proceed to wash hands in an unmonitored fashion. In one contemplated embodiment, when continued hand-washing is detected, the compliance system 100 can continue to update the total scrubs meter 322 and may transition the time meter 308 from a countdown timer to a total time display so that the user is still informed as to how long they have been washing their hands.

Further, when the finish step 932 is invoked, the compliance system 100 may provide a "compliance complete" signal to the user. Further, the finish step 932 can provide the user with instructions to dry their hands and apply hand lotion.

It is contemplated that a graphical representation of lotion or a lotion dispenser can be shown on the user interface 104 of FIG. 1 to encourage the user to proceed with moisturizing their hands to avoid dermatitis. Further it is contemplated that a light attached to the hand lotion dispenser could flash, thereby providing additional stimuli to the user that encourages the use of moisturizer.

By encouraging the use of moisturizer the compliance system 100 may encourage long term compliance by preventing hand discomfort that may occur due to dryness which has an increased chance of occurring when hand-washing is performed more frequently.

Figure 10:
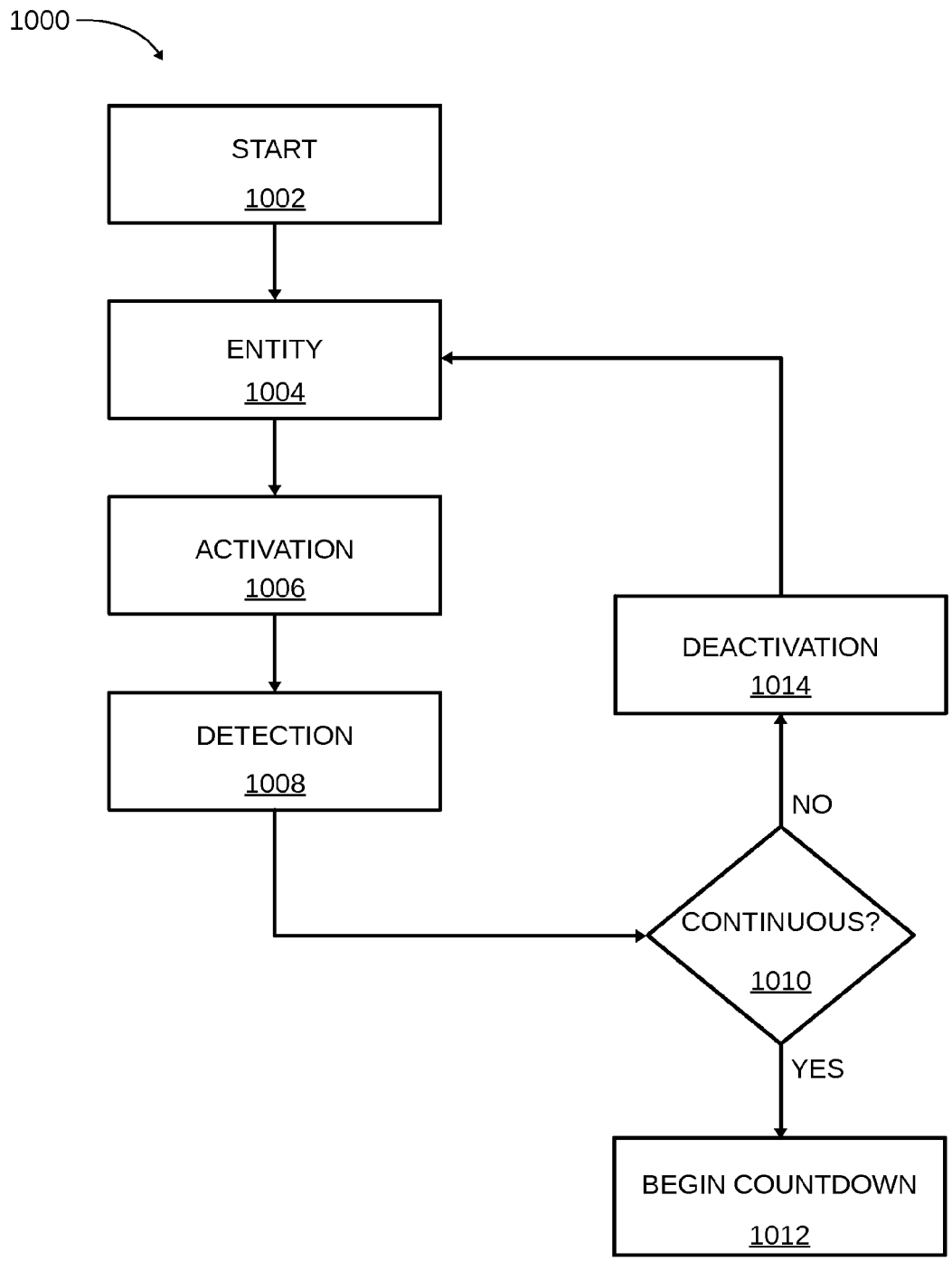
FIG. 10 is a control flow for power management of the compliance system of FIG. 1.

Referring now to FIG. 10, therein is shown a control flow 1000 for power management of the compliance system 100 of FIG. 1. Control flow 1000 depicts a process whereby the compliance system 100 negotiates between a low power state and a high power state in order to conserve power over the lifetime of the compliance system 100.

It has been discovered that the process depicted in the control flow 1000 is advantageous to embodiments dependent upon batteries or low power generation such as generation of power by turbine integrated into the sink piping. In embodiments where a pipe-integrated micro turbine generates power from water flowing down the sink, water only flows down the drain a small percentage of the time so the total power generation of a pipe-integrated micro turbine is low.

However by transitioning between low power and high power states it has been discovered that the compliance system 100 is able to maintain low power in order to accommodate such a configuration. Upon the activation of the high power state and the continuous detection of vigor and scrubs the compliance system 100 enters into the control flow depicted in FIG. 11, which in this contemplated embodiment, constitutes the beginning a countdown game.

The control flow 1000 is shown beginning with a start step 1002. The start step 1002 indicates the beginning of the control flow 1000 and can initiate an entity detection step 1004.

The entity detection step 1004 can utilize the low power sensors 212 of FIG. 2 on the compliance system 100 to detect whether any new users are detected within an observation area. The low power sensors 212 can be motion sensors with a fresnel lens and a pair of comparator-based single-pixel thermal sensors, commonly referred to as a passive infrared sensor, or "PIR".

The low power sensors 212 may remain deactivated and unpowered most of the time if the initialization time of the sensor is sufficiently low. For example if the sensor has a 50 millisecond boot time and a response time for high power-up of 1 second is satisfactory, then the low power sensors 212 may remain deactivated and unpowered 105% of the time if it is activated once per second.

In this exemplary illustration, the compliance system 100 would have a mean response time of 0.525 seconds and a worst case response time of 1 second. Furthermore a low power processor may enter a low power state and wake up only once per second if the wakeup time is sufficiently rapid.

The compliance system 100 is contemplated to include the processor 120 of FIG. 1, which can be a low power processor and can wake up in 50 milliseconds (ms). After the processor 120 wakes up, the processor 120 can be used to wake up the low power sensors 212, which is contemplated to require 50 ms to collect a sensor reading. It is contemplated an additional 50 ms are required to process the reading from the low power sensors 212 and to determine whether a high power mode should be entered into.

It has been discovered that the low power sensors 212 in combination with the processor 120 would have a minimum response time of 150 ms, a maximum response time of 1 second, and an average response time of 5.75 seconds if activated once per second. Such a response time may be quite adequate and result in a power savings of 100% or more, depending on the power consumption while the low power processor is sleeping.

If an entity is detected during the entity detection step 1004 within the sensor area of the low power sensors 212 then the sensors 106 of FIG. 1 can be activated along with the processor 120 in an activation step 1006. It is contemplated that the sensors 106 can be a high power sensor. It is further contemplated that the processor 120 can have a low power and high power processing functionality or multiple processors can be used.

Successful completion of the activation step 1006 can activate a detection step 1008. During the detection step 1008, the data from the sensors 106 can be analyzed in real time to detect vigor and scrubs.

It is contemplated that in one embodiment the processor 120 can execute at 10 megahertz (MHz) monitoring when monitoring the low power sensors 212 and maintaining a sleep state for the majority of the time during the entity detection step 1004. When the low power sensors 212 detect that a user has entered the sensing area, the processor 120 can execute at 1 gigahertz (GHz) and the sensors 106 can be brought into a powered-up state from a sleep state.

During the detection step 1008 vigor and scrubs of a user may be detected by performing change detection analysis. The processor 120 can compare a previous reading from the sensors 106 with a current reading of the sensors 106.

The aggregation of absolute differences may be used as an overall estimate of change. Alternatively only differences in one direction such as differences resulting from a sensor value going from a lower level to a higher level may be used to contribute to the aggregation and the differences going in the other direction may be discarded.

The direction of change can be used to indicate the current state of scrubbing motion. It has been discovered that readings from the sensors 106 collected over a multi-sample period, such as 18 recordings taken over 2 seconds from a 10 Hz camera, can be used in an analysis and to determine if a rhythm is present in the number of times the sensors 106 detect transitions between a high and low state.

The number of transitions detected by the sensors 106 may be used as a measure of vigor, where a small number of transitions between high and low motion may be used to indicate low vigor as described below with regard to the detection thresholds of FIG. 15. If a high number of transitions are detected indicating sufficient vigor, the control flow of the compliance system 100 will continue vigor for T_Start seconds.

If the vigor is detected for more than T_Start seconds, the compliance system 100 will recognize the vigor as continuous in a continuous decision step 1010. When the vigor is recognized as continuous in the continuous decision step 1010, a result of "YES" will prompt the compliance system 100 to activate the countdown game of FIG. 11 in a begin countdown step 1012.

If the vigor is not detected for more than T_Start seconds, the compliance system 100 will recognize the vigor as not continuous in the continuous decision step 1010. When the vigor is recognized as not continuous in the continuous decision step 1010, a result of "NO" will prompt the compliance system 100 to deactivate the high power monitoring of the sensors 106 in a deactivation step 1014.

The deactivation step 1014 will place the compliance system 100 back into the low power mode of the entity detection step 1004. In one contemplated embodiment the T_Start second limit can be one second or two seconds.

Figure 11:
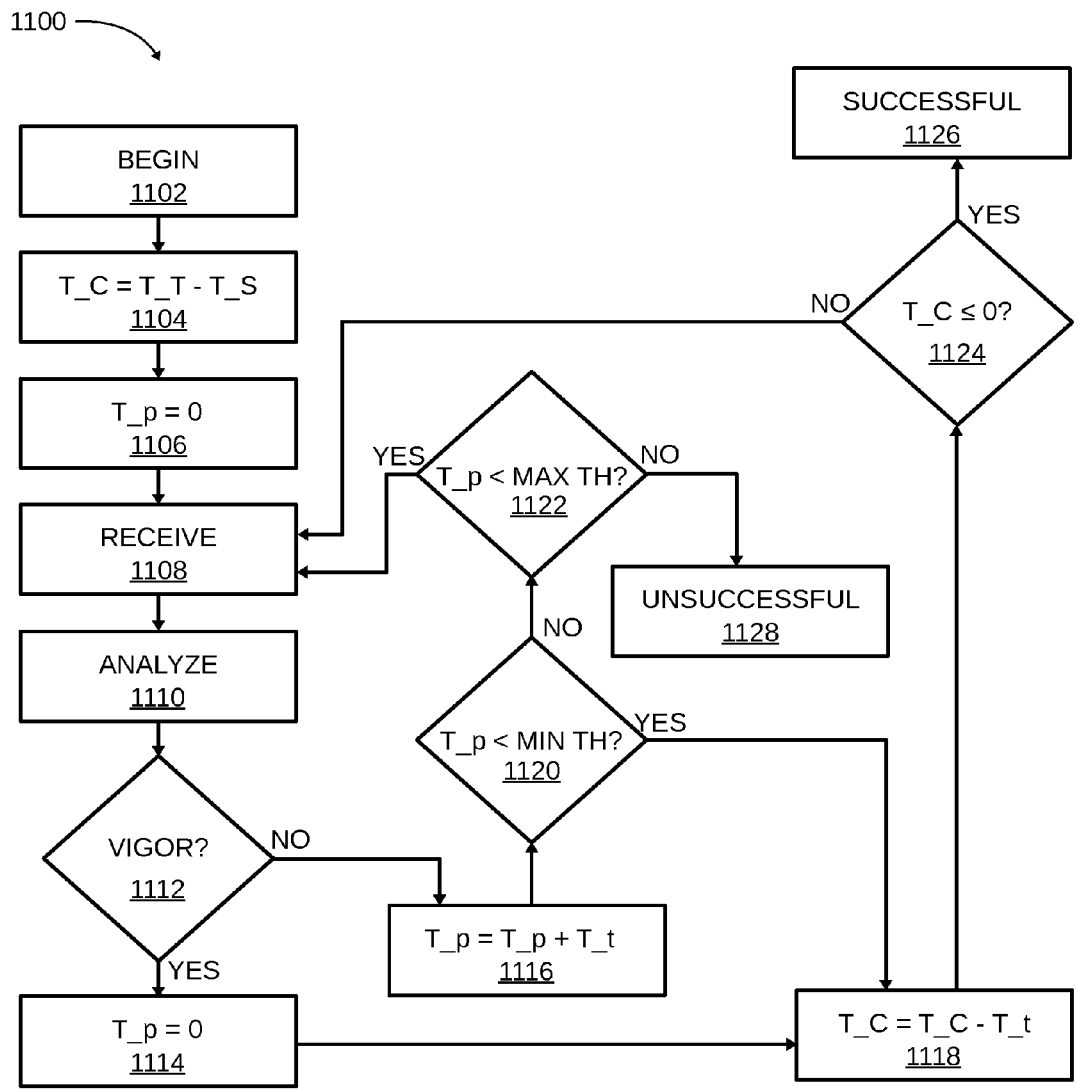
FIG. 11 is a control flow for a conditional count down for the compliance system of FIG. 1.

Referring now to FIG. 11, therein is shown a control flow 1100 for a conditional count down for the compliance system 100 of FIG. 1. The control flow 1100 depicts a countdown game or sensor analysis-driven conditional countdown.

The control flow 1100 can monitor the vigor of hand-washing and enters a paused or a reset mode depending on when vigor is detected and when it is not detected. It is contemplated that the control flow 1100 can be performed in a high power state activated by the activation step 1006 of FIG. 10 where the sensors 106 of FIG. 1 and the processor 120 of FIG. 1 runs in a high power mode.

The control flow 1100 is shown beginning with a begin countdown step 1102. The begin countdown step 1102 indicates the beginning of the control flow 1100 can correspond to the begin countdown step 1012 of FIG. 10. The begin countdown step 1102 can initiate a set T_Current step 1104.

The set T_Current step 1104 can set the variable T_Current to T_Total minus T_Start. In the set T_Current step 1104 a value is stored in a variable T_Current. The new value stored in T_Current is derived by subtracting a variable T_Start from T_Total.

T_Total can be the length of time over which vigorous hand-washing would suggest a compliant hand-wash. As an illustrative example, values for T_Total could be 20 seconds and could identify that a compliant hand-wash must have vigorous hand-washing detected for at least 20 seconds.

The value for T_Total could be other values as well such as: 30 seconds, 40 seconds, 1 minute, or other desired amounts of time. It is contemplated that a particular vigor-aware sink may be configured with a T_Total of 3 minutes if the sink is commonly used by hospital workers that wash their hands very rigorously before proceeding to their next task. It is contemplated that the desired length represented by T_Total could be a set individually for specific each user. It is contemplated that the compliance system 100 could identify specific users by speech recognition, gesture recognition, face recognition, or a multimodal combination.

The variable T_Start corresponds to the amount of time during which vigorous hand-washing is estimated to already have occurred. For example if the activation step 1006, the detection step 1008 of FIG. 10, the continuous decision step 1010 of FIG. 10, and the begin countdown step 1012 take one second to execute and wake up the sensors 106 and the processor 120 during which time the sensors 106 is unlikely to detect the user's vigorous hand-washing, T_Start may be set to a time of 1 second.

In contrast when the compliance system 100 is operating in a continuous high power setting or the sensors 106 identify vigorous hand-washing immediately, T_Start might be set significantly lower or even to zero. Completion of the set T_Current step 1104 can initiate the execution of a set T_pause step 1106.

The set T_pause step 1106 initializes the T_pause variable to zero. The T_pause variable stores the length of time during which the compliance system 100 estimates the user may not have been washing vigorously.

The T_pause variable will be updated later on in the control flow 1100 and used to determine whether countdown timer 922 of FIG. 9 and graphically depicted in the time meter 308 of FIG. 3 or the individual time meter levels 310 of FIG. 3, should be paused or even reset. Once the set T_pause step 1106 has been executed, a receive data step 1108 can be initiated.

In the receive data step 1108 real-time data arrives at the processor 120 from the sensors 106 ready for analysis. The data represents what has been detected by the sensors 106 over the last T_tick seconds. An example value of T_tick might be 0.03333 seconds, such as in the case of a sensor that collects 30 frames per second. Other examples for T_tick are 0.125 seconds or 0.1111 seconds which might be used with a thermal sensor collecting data at 8 Hz or 9 Hz, respectively.

The data received in the receive data step 1108 can be analyzed in an analyze data step 1110. The analyze data step 1110 can implement the processor 120 to analyze the data collected previously. As an example, the processor 120 can analyze the data received from the sensors 106 during previous executions of the receive data step 1108 along with the data received from the sensors 106 during the most recent execution of the receive data step 1108.

The analysis of the data from the sensors 106 enables a determination of whether vigor was detected in a vigor detection decision step 1112. The vigor detection decision step 1112 can branch the control flow 1100 path based on whether the data of the sensors 106 is likely to have been caused by vigorous washing action or by something else.

It is contemplated that the previous data analyzed during the analyze data step 1110 can be stored as a variable such as x. It is contemplated that the variable x could represent the previous portions of data received. An example value for x could be 18 in the case that the most recent 2 seconds of data are being analyzed for vigor detection and the sensor is reading data at 9 Hz.

When it is determined that sufficient vigor is being sensed, the vigor detection decision step 1112 will return a "YES". A YES result from the vigor detection decision step 1112 can invoke a zero T_pause step 1114.

When it is determined that sufficient vigor is not being sensed, the vigor detection decision step 1112 will return a "NO". A NO result from the vigor detection decision step 1112 can invoke an increase T_pause step 1116.

The zero T_pause step 1114 is reached in the case that the most recent attempt to detect vigor in the vigor detection decision step 1112 and the analyze data step 1110 resulted in positive detection of vigor. In this case T_pause is set to 0 which has the effect of pushing back the point at which the compliance system 100 may enter the paused state, for example the pause step 928 of FIG. 9 during which countdown ceases, to at least a minimum pause threshold.

Completion of the zero T_pause step 114 can initiate the decrease T_Current step 1118. When the vigor detection decision step 1112 determines that no vigor was detected during the most recent executions of the vigor detection decision step 1112 and the analyze data step 1110, the increase T_pause step 1116 can be initiated.

During the increase T_pause step 1116 the T_pause variable is set to the sum of its previous value plus T_tick. For example, if this is the first time the compliance system 100 has entered the increase T_pause step 1116 then the previous value for T_pause will be zero. Continuing the example, if T_tick is equal to 0.125 then the new value of T_pause will be 0.125.

After the execution of the increase T_pause step 1116 a minimum pause threshold decision step 1120 can be initiated. The minimum pause threshold can be a time setting threshold that must be exceeded to trigger the paused condition and stop the countdown.

The minimum pause threshold could, for example, be 2 seconds. If vigor has not been detected in the vigor detection decision step 1112 during the last 2 seconds, under this example, the countdown timer 922 would be paused.

The minimum pause threshold decision step 1120 can determine whether the compliance system 100 is in a paused state. Determination of the paused state is accomplished by comparing T_pause to the minimum pause threshold.

If T_pause is less than the minimum pause threshold then the compliance system 100 is not in the paused state and the minimum pause threshold decision step 1120 will return a "YES". When a YES result is obtained from the minimum pause threshold decision step 1120, the decrease T_Current step 1118 can be invoked.

If T_pause is greater than or equal to the minimum pause threshold then the compliance system 100 is in the paused state and the minimum pause threshold decision step 1120 will return a "NO". When a NO result is obtained from the minimum pause threshold decision step 1120, a maximum pause threshold decision step 1122 can be invoked.

The decrease T_Current step 1118 performs the countdown step by decreasing T_Current. T_Current represents the current remaining time in the hand-wash. The decrease T_Current step 1118 decreases T_Current from its previous value to its previous value minus T_tick. For example if its previous value of T_Current was 15 seconds and T_tick is equal to 0.125 seconds then the new value for T_Current set in the decrease T_Current step 1118 is 14.875.

Once T_Current has been decreased in the decrease T_Current step 1118, a T_Current zero decision step 1124 can be initiated. The T_Current zero decision step 1124 can determine whether the hand-wash countdown is complete.

When the T_Current zero decision step 1124 determines that T_Current is less than or equal to zero a "YES" result is returned. When a YES is returned from the T_Current zero decision step 1124 a successful step 1126 can be invoked. The successful step 1126 signifies to the user that the game has been completed successfully.

When the T_Current zero decision step 1124 determines that T_Current is greater than zero a "NO" result is returned. When a NO is returned from the T_Current zero decision step 1124 the receive data step 1108 can be invoked and the countdown continues with the loop from the T_Current zero decision step 1124 to the receive data step 1108.

The maximum pause threshold decision step 1122 is reached when the compliance system 100 is in the paused state and the minimum pause threshold decision step 1120 returns a NO. The maximum pause threshold decision step 1122 can compare the T_pause variable, which represents the length of time that the process has been in the paused state, to a maximum pause threshold.

When T_pause is greater than or equal to the maximum pause threshold then the maximum pause threshold decision step 1122 will return a "NO". When a NO result is obtained by the maximum pause threshold decision step 1122 an unsuccessful step 1128 is invoked. The unsuccessful step 1128 signifies to the user that the game has not been completed successfully.

When T_pause is less than the maximum pause threshold then the maximum pause threshold decision step 1122 will return a "YES". When a YES result is obtained by the maximum pause threshold decision step 1122, the receive data step 1108 is invoked and completes a loop from the maximum pause threshold decision step 1122 to the receive data step 1108.

It is contemplated that when the transition from the maximum pause threshold decision step 1122 to the receive data step 1108 is taken, it is not too late for the user to resume scrubbing and continue the countdown process without starting over.

In one contemplated embodiment the minimum pause threshold could be less than or equal to the maximum pause threshold to represent the condition that a reset is only performed after the paused state is entered into. In this contemplated embodiment a NO result from the T_Current zero decision step 1124 indicating that T_Current is greater than zero could invoke the maximum pause threshold decision step 1122 rather than the receive data step 1108.

It is contemplated that this alternative embodiment could result in a more efficient implementation because it could allow for a more compressed program, which might thereby result in the ability to use a lower power computer to perform the control flow 1100.

Figure 12:
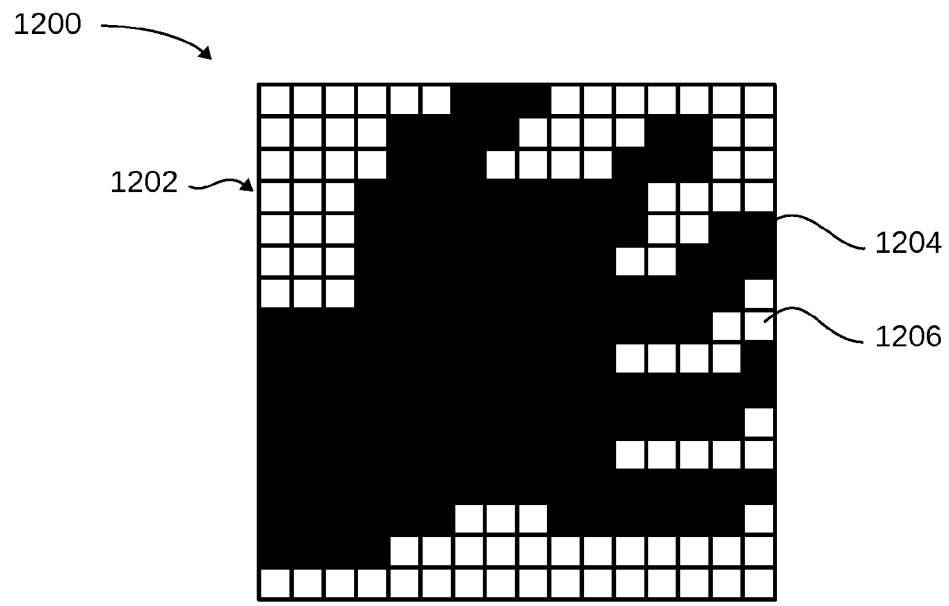
FIG. 12 is a graphical view of an initial image captured by the sensors of FIG. 1.

Referring now to FIG. 12, therein is shown a graphical view of an initial image 1200 captured by the sensors 106 of FIG. 1. The initial image 1200 can be an initial sensor reading at a discrete time and is shown having pixels 1202.

The pixels 1202 are shown as black pixels 1204 in the shape of a hand and white pixels 1206 around the black pixels 1204. The black pixels 1204 depict the shape of a human hand while the white pixels 1206 depict the background.

For descriptive clarity the initial image 1200 will be discussed in terms of an image captured with a thermal imaging camera, it is contemplated that the techniques may be adapted to work with other types of imagery such as color camera imagery. Imagery that is directly output from a thermal camera, such as the sensors 106, may have the value of each of the pixels 1202 represented in degrees Kelvin with some number of decimal places depending on the accuracy of the sensors 106.

One way of depicting the sensors 106 imagery that represents thermal values is to assign the pixels 1202 that are increasingly dark to a hotter temperature, which is the so called "black hot" image representation. Temperature differences can be represented by different shades of gray. It is contemplated that the initial image 1200 does not depict any gray values because it has been processed by the processor 120 of FIG. 1 to determine those exact pixels which belong to human hand shown as the black pixels 1204, and which do not shown as the white pixels 1206.

It is contemplated that the processing of the initial image 1200 may be performed by using a stationary camera for the sensors 106 with a background that is not moving. The sensors 106 may then take a picture of the background and store it as a background thermal image while no hand is present. The background thermal image may be stored in memory for use in processing subsequent imagery which may have human or other warm-bodied object present.

A method of determining which of the pixels 1202 belong to a warm-bodied object is to subtract the background thermal image stored in memory from values of the current image, such as the initial image 1200, for each of the pixels 1202. A positive result for any of the pixels 1202 indicates that the specific pixel 1202 is warmer now than was detected in the background thermal image and may indicate that the pixel 1202 is landing on or detecting a human hand or other warm object.

It contemplated that this detection of a warm body might have some noise as the temperature of the background thermal image is known to fluctuate. To eliminate noise, a filter may be used. It is contemplated that one such filter may have a lower filter threshold and that only the pixels 1202 that differ from the background thermal image more than the lower filter threshold will be recognized by the compliance system 100 as representing a human hand.

It is contemplated that any of the pixels 1202, which do not differ from the background thermal image more than the lower filter threshold value, will not be recognized by the compliance system 100 as representing a human feature. Illustratively, one contemplated value for the lower filter threshold may be 3 degrees Celsius.

It is contemplated that the background thermal image may be updated from time to time in order to compensate for systemic error such as may be present in thermal cameras that lack active cooling. For example, the temperature of a thermal camera can indicate how it perceives the temperature of each pixel it senses.

As one example it is possible for a thermal camera to believe that pixels are getting hotter when in fact they land on objects that are the same temperature. This type of error can be introduced by the heating-up of the camera.

Updating the background thermal image from time-to-time when no warm bodies are present, can correct for such fluctuations. It has been discovered that compensating the sensors 106 by updating the background thermal image can be valuable for cameras that lack alternative calibration methods such as physical shutter calibration.

Figure 13:
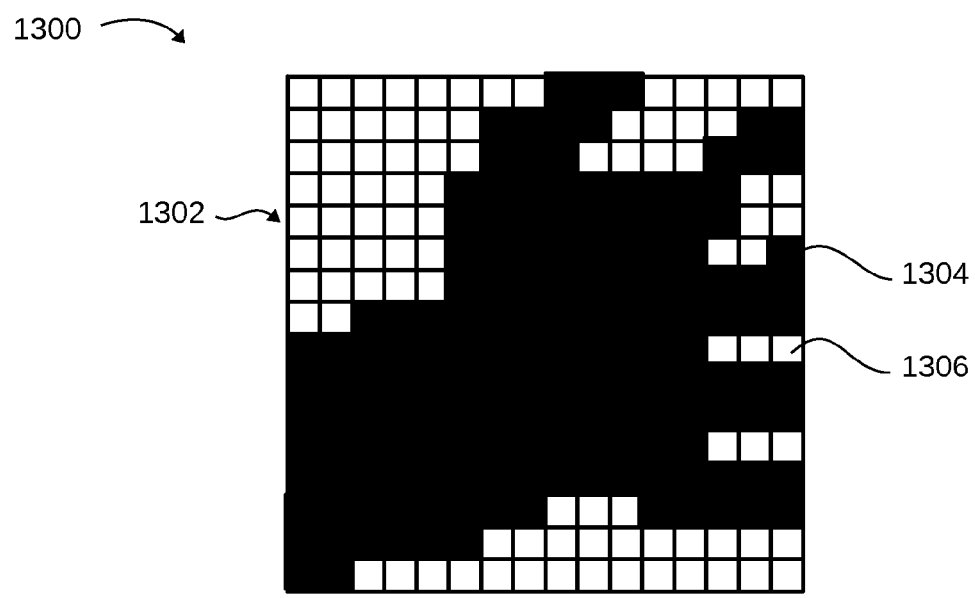
FIG. 13 is a graphical view of a subsequent image captured by the sensors of FIG. 1.

Referring now to FIG. 13, therein is shown a graphical view of a subsequent image 1300 captured by the sensors 106 of FIG. 1. The subsequent image 1300 is a sensor reading captured at a discrete time subsequent to the initial image 1200 of FIG. 12. The initial image 1200 can be considered a previous frame in reference to the subsequent image 1300.

The subsequent image 1300 is shown having pixels 1302 including black pixels 1304 and white pixels 1306. The subsequent image 1300 shows the black pixels 1304 depicting a hand shifted right.

The rightward shift of the black pixels 1304 can indicate that the hand detected in the initial image 1200 has moved to the right. The subsequent image 1300 further depicts less of the black pixels 1304 that correspond to fingers of the hand shown in the initial image 1200 and more of the black pixels 1304 that correspond to a wrist of the user.

It is contemplated that other embodiments can be implemented without requiring the capture and storage of the background thermal image as discussed above with regard to FIG. 12. It has been discovered that when it is desirable to estimate the amount of movement that a warm body is undergoing over time in the field of view of the sensors 106, the background thermal image is not required to be stored but instead the compliance system 100 may rely on a previous image, such as the initial image 1200.

In such a contemplated embodiment, the initial image 1200 might be stored and subtracted from the subsequent image 1300, to identify only the pixels 1302 that are hotter in the subsequent image 1300 than the pixels 1202 of FIG. 12 in the initial image 1200. The number of the pixels 1302 that differ, more than the lower filter threshold, in the subsequent image 1300 from the pixels 1202 in the initial image 1200 can be regarded by the compliance system 100 as movement of the warm body in front of the sensors 106.

Figure 14:
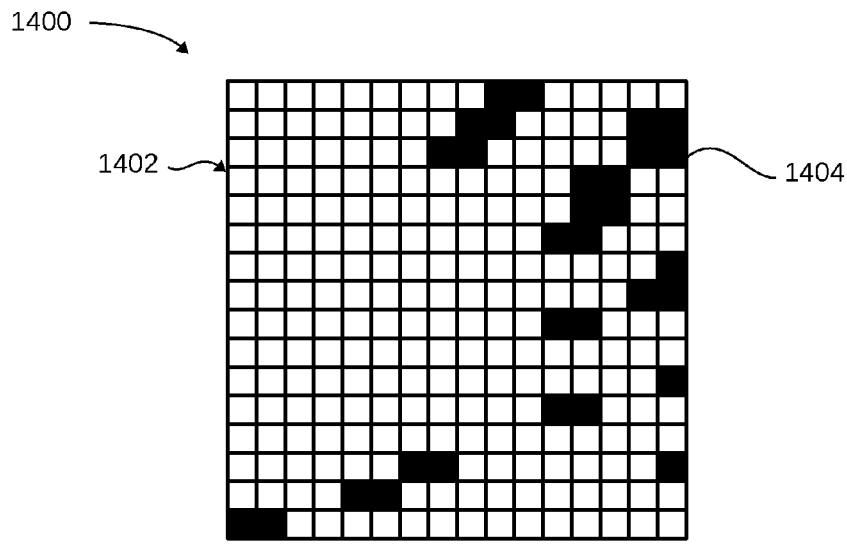
FIG. 14 is a graphical view of a difference image between the initial image of FIG. 12 and the subsequent image of FIG. 13.

Referring now to FIG. 14, therein is shown a graphical view of a difference image 1400 between the initial image 1200 of FIG. 12 and the subsequent image 1300 of FIG. 13. The difference image 1400 can show pixels 1402 as a result of identifying the white pixels 1206 of FIG. 12 and that changed to the black pixels 1304 of FIG. 13.

It can be seen from the subsequent image 1300 that when the sensors 106 of FIG. 1 captured the subsequent image 1300 the hand depicted in the initial image 1200 had moved to the right within the frame of the sensors 106. Black or newly hot pixels can represent movement estimations 1404.

The movement estimations 1404 can correspond to the white pixels 1206 of the initial image 1200 that were not hot enough to be estimated as part of a warm body but increased in temperature to be classified as the black pixels 1304 of the subsequent image 1300 when they were hot enough to be estimated as representing the warm body.

The movement estimations 1404 can be calculated based on the movement of the hand from left in the initial image 1200 to right in the subsequent image 1300. It can be seen that the fingers that are orthogonal (at a right degree angle from) the direction of motion result in the most detection of the movement estimations 1404.

The total number of the movement estimations 1404 can be an estimate of motion for the user. It is contemplated that once the difference between the pixels 1202 of FIG. 12 and the pixels 1302 of FIG. 13 is calculated, the compliance system 100 can isolate only the newly hot pixels when determining the movement estimations 1404.

It is contemplated that the pixels that changed their value from the black pixels 1204 of FIG. 12 to the white pixels 1306 of FIG. 13 will not be registered within difference image 1400 or regarded as the movement estimations 1404 since such pixels are not newly hot but are more aptly termed newly cold pixels; therefore, the movement estimations 1404 are isolated only to differences that are based on movement of warm objects.

When two warm bodies, such as two human hands, move from not occluding each other in the image to occluding the number of the pixels 1402 that are estimated to be the movement estimations 1404 may be few since the increase in occlusion means fewer pixels will be representing a hot body that is because the surface area of the detected objects decreases due to occlusion.

It has been discovered that by calculating the movement estimations 1404 as newly hot pixels rather than just changed pixels the change in a polarity can be detected, which is valuable because it can be used to determine the phase within a repetitive motion, such as the position of hands engaged in a scrubbing motion and the phase within the scrubbing cycle that those hands are in.

It is contemplated that a newly cold pixel count can be compared to the black pixel 1404 count in order to further determine a phase of motion for the hands of a user. It has been discovered that comparing the newly cold pixels with the movement estimations 1404 can also be used for determining the kind of motion being performed (e.g. non-occluding).

It is contemplated that the amount of motion can be represented by the movement estimations 1404 alone or, in the alternative, by the number of the movement estimations 1404 plus newly cold pixels. The difference image 1400 is shown having 31 of the movement estimations 1404.

Figure 15:
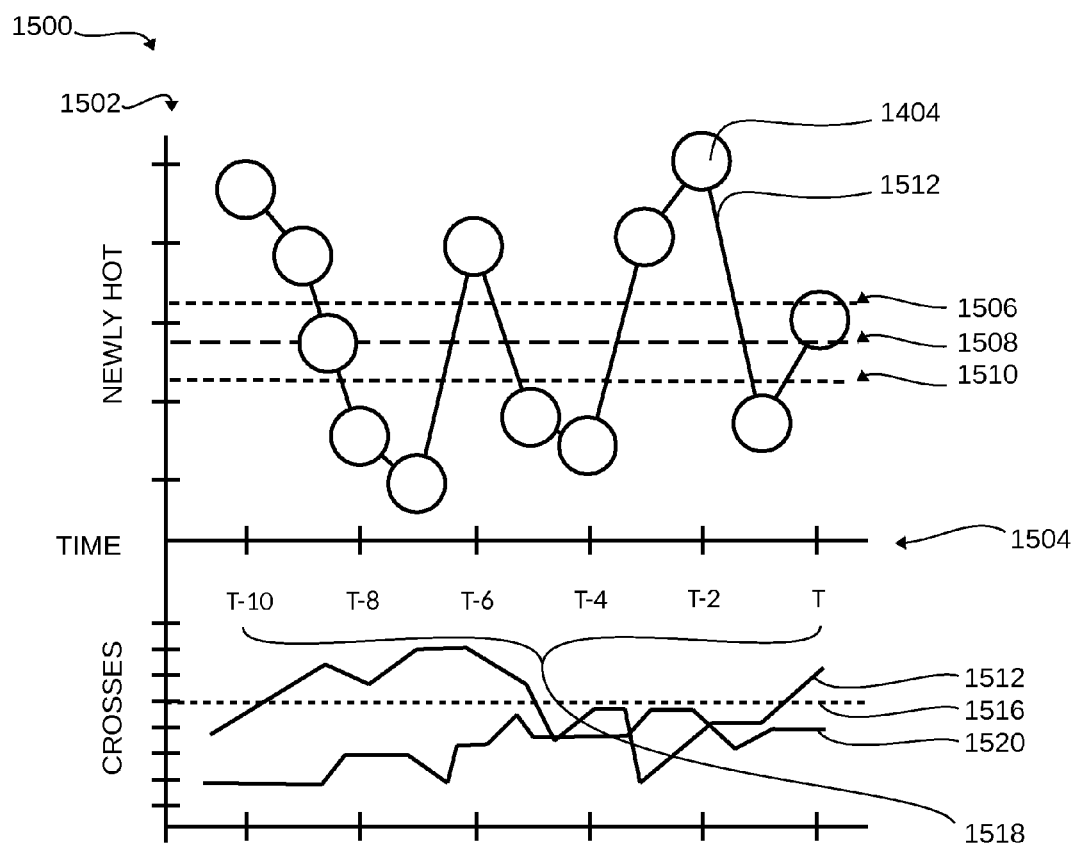
FIG. 15 is a graphical view of a chart for determining the vigor for the compliance system of FIG. 1.

Referring now to FIG. 15, therein is shown a graphical view of a chart 1500 for determining the vigor for the compliance system 100 of FIG. 1. The chart 1500 depicts graphically a method of calculating the vigor of a hand-wash by using the count of the movement estimations 1404 of FIG. 14, which indicate newly hot pixels measured over time.

The y-axis 1502 of the chart 1500 corresponds to the number of the movement estimations 1404. The x-axis 1504 corresponds to time. The current time is T, which is the rightmost position of the graph, represented by the "T" label on the x-axis 1504. Example units for time are contemplated to be tenths of a second, such that the data point positioned at time T-10 represents data collected one second prior to the current time.

The chart 1500 is shown having an upper threshold 1506, an average 1508, and a lower threshold 1510. The upper threshold 1506, the average 1508, and the lower threshold 1510 can be used to analyze the movement estimations 1404 for determining a frequency, or rate of repetition, of hand-washing. The chart 1500 is further depicted with a chart line 1512 connecting the movement estimations 1404 that are calculated at each time increment along the x-axis 1504.

It is contemplated that one embodiment could include the upper threshold 1506 and the lower threshold 1510 being equal to the average 1508. It is contemplated that when the upper threshold 1506 and the lower threshold 1510 are equal to the average 1508 the analysis of the movement estimations 1404 may proceed by counting crosses such as the line crosses 1514. The line crosses 1514 can be the number of times the chart line 1512 crosses the average 1508.

As can be seen in the chart 1500, the line crosses 1514 can be counted or detected a total of six times. When the upper threshold 1506 and the lower threshold 1510 are equal to the average 1508, one method of determining the number of scrubbing repetitions utilizes the assumption that the hands occlude each other twice during a single repetition.

The occlusions occur once where the left hand is moving forward, and once where the right hand is moving forward. These occlusions are detected as a lower number of the movement estimations 1404, which appear below the average 1508. In contrast, as the hands move out from the occlusion and the forward hand covers more area of the frame of the sensors 106 of FIG. 1, the number of the movement estimations 1404 increases significantly, which appears as a detection above the average 1508.

The average 1508 may be derived as the average of the movement estimations 1404 recorded over a certain period of time, such as 1 or two seconds. It has been discovered that when a user's scrubbing style changes, the amount of motion for the new style generally has a smaller rise and fall in the movement estimations 1404 so it could be detected as a lack of motion. That is, a lack of the movement estimations 1404 transitioning through the average 1508.

Conversely when a user changes scrubbing motions and the movement estimations 1404 increases the scrub may result in many readings above the average 1508. In both scenarios where the user's scrubbing motion changes, the compliance system 100 may erroneously identify the scrub as having stopped.

One solution that has been discovered to detect scrubs, when the user changes hand-washing motions, is to detect a pause in the scrubbing motion only if the line crosses 1514 that are detected fall below a cross-threshold 1516 for a specified time 1518. The specified time 1518 can be the same or longer than the timespan that the current hand scrub state is analyzed over.

For example, if the chart line 1512 is being analyzed over a timespan of 1 second, as is the case for the chart 1500, then the compliance system 100 may continue to perform countdown with the countdown timer 922 of FIG. 9 for the specified time 1518 of one or two seconds even though the line crosses 1514 falls below the cross-threshold 1516. If the line crosses 1514 falls below the cross-threshold 1516 longer than the specified time 1518, it can be recognized by the compliance system 100 that the detected scrubbing exceeding the minimum pause threshold, which can be the same threshold used in the minimum pause threshold decision step 1120 of FIG. 11. When the minimum pause threshold is exceeded then the compliance system 100 may pause the countdown of the countdown timer 922 in anticipation of a resumption of scrubbing vigor.

The line crosses 1514 may thus be used as a measure of vigor and the cross-threshold 1516 can represent a minimum level of vigor that must be maintained to ensure the countdown timer 922 continues without pause. The average 1508 may be derived by the processor 120 of FIG. 1 as the average of the movement estimations 1404 present in the analysis timespan (T through T-10). It is contemplated that an analysis of 1 or 2 seconds or some other amount of time may be used.

The analysis timespan can be a sliding window, for calculating the average 1508 as well as calculating the line crosses 1514. It has been discovered that in some scenarios noise can trigger or increase the detection of the line crosses 1514.

The increase in the number of times the compliance system 100 detects the line crosses 1514 due to noise can be compensated for by implementing the upper threshold 1506 and the lower threshold 1510 that are not equal to the average 1508. It is contemplated that the number of times the chart line 1512 transitions from above the upper threshold 1506 to below the lower threshold 1510, or transitions from below the lower threshold 1510 to above the upper threshold 1506 during consecutive movement calculations can be counted as crosses such as threshold crosses 1520.

Further, it is contemplated that the chart line 1512 does not need to transition from one estimation of the movement estimations 1404 through both the upper threshold 1506 and the lower threshold 1510 to a next estimation of the movement estimations 1404, but the threshold crosses 1520 may still be counted even if intermediate estimations of the movement estimations 1404 fall between the upper threshold 1506 and the lower threshold 1510. It has been discovered that the upper threshold 1506 and the lower threshold 1510 beneficially reduce the false detection of vigor.

It is contemplated that implementing the upper threshold 1506 and the lower threshold 1510 for noise filtering can include estimating the movement estimations 1404 from oldest to newest (left to right in the chart 1500). A variable S will be set as soon as the movement estimations 1404 are estimated to be above the upper threshold 1506 or below the lower threshold 1510. If the first estimation of the movement estimations 1404 not falling between the upper threshold 1506 and lower threshold 1510 is above the upper threshold 1506 then variable S can be set to "Upper". If the first estimation of the movement estimations 1404 not falling between the upper threshold 1506 and lower threshold 1510 is below the lower threshold 1510 then variable S is set to "Lower".

The variable S may be set to "Upper" or "Lower" whenever the movement estimations 1404 are estimated above the upper threshold 1506 or below the lower threshold 1510, respectively. Whenever the variable S transitions from "Upper" to "Lower" or "Lower" to "Upper" the threshold crosses 1520 is incremented. It is contemplated that when the movement estimations 1404 are estimated between the upper threshold 1506 and the lower threshold 1510 the value of the variable S is not changed. It is further contemplated that a number of crosses can be incremented by either the threshold crosses 1520 or the line crosses 1514.

Thus, it has been discovered that the compliance system furnishes important and heretofore unknown and unavailable solutions, capabilities, and functional aspects. The resulting configurations are straightforward, cost-effective, uncomplicated, highly versatile, accurate, sensitive, and effective, and can be implemented by adapting known components for ready, efficient, and economical manufacturing, application, and utilization.

While the compliance system has been described in conjunction with a specific best mode, it is to be understood that many alternatives, modifications, and variations will be apparent to those skilled in the art in light of the preceding description. Accordingly, the compliance system is intended to embrace all such alternatives, modifications, and variations, which fall within the scope of the included claims. All matters set forth herein or shown in the accompanying drawings are to be interpreted in an illustrative and non-limiting sense.

What is claimed is:

1. A method for managing hand-wash compliance comprising:
    acquiring a background image;
    acquiring thermal images including an initial thermal image and a subsequent thermal image;
    determining hot pixels of the thermal images belonging to a warm-bodied object by:
        subtracting the background image from the thermal images, and
        filtering out pixels of the thermal images being below a thermal threshold from the background image;
    estimating a user's hand-wash motions, the user's hand-wash motions being estimated by determining a change in the hot pixels between the initial thermal image and the subsequent thermal image;
    estimating hand-wash scrubs per minute based on the user's hand-wash motions;
    counting a total hand-wash scrubs based on the user's hand-wash motions;
    estimating hand-wash vigor based on a number of transitions between high and low motions;
    calculating a hand-wash score based on the hand-wash vigor;
    displaying the hand-wash vigor, the total hand-wash scrubs, and the hand-wash scrubs per minute on a display;
    displaying a timer that counts down based on the hand-wash vigor; and
    updating the background image based on the warm-bodied object being absent from the thermal images.

2. The method of claim 1, wherein displaying the hand-wash vigor includes:
    displaying a minimum vigor compliance indicator in red,
    displaying a high vigor compliance indicator in yellow,
    displaying a highest vigor compliance indicator in green; or
    displaying a combination thereof.

3. The method of claim 1, wherein calculating the hand-wash score based on the hand-wash vigor includes:
    decreasing the hand-wash score based on the hand-wash vigor being estimated as a minimum vigor compliance;
    increasing the hand-wash score based on the hand-wash vigor being estimated as a high vigor compliance; and
    increasing the hand-wash score, based on the hand-wash vigor being estimated as a highest vigor compliance, and the increase based on the hand-wash vigor being estimated as the highest vigor compliance being faster than the hand-wash score increased based on the hand-wash vigor being estimated as the high vigor compliance.

4. The method of claim 1, wherein displaying the timer that counts down based on the hand-wash vigor includes pausing the timer when the hand-wash vigor is estimated to be below a threshold.

5. The method of claim 1, further comprising:
    determining a high score based on the hand-wash score for: a prior day, a prior week, a prior month, a prior year, and all time; and
    displaying the high score for: the prior day, the prior week, the prior month, the prior year, and all time only when a full time period of the determination of the high score has elapsed.

6. The method of claim 1, further comprising displaying options to: add a user, delete the user, view the user's historical data, view multiple users, and view use and compliance statistics.

7. The method of claim 1, further comprising:
    displaying the total hand-wash scrubs counted for each day of a current week; and
    displaying the hand-wash score calculated for each of the days of the current week.

8. The method of claim 1, further comprising:
    displaying multiple users in rows; and
    displaying a role, the hand-wash scrubs per minute, the total hand-wash scrubs, and the hand-wash score for each of the multiple users.

9. The method of claim 1, further comprising displaying statistical calculations of the hand-wash scrubs per minute, the total hand-wash scrubs, the hand-wash vigor, the hand-wash score, the timer, or a combination thereof.

10. The method of claim 1, wherein displaying the hand-wash vigor, the total hand-wash scrubs, and the hand-wash scrubs per minute, and the timer includes displaying the hand-wash vigor, the total hand-wash scrubs, and the hand-wash scrubs per minute, and the timer only after a user has been detected to be within a vicinity of a sensor.

11. A non-transitory computer readable medium, useful in association with a processor, including instructions configured to:
    acquire a background image;
    acquire thermal images including an initial thermal image and a subsequent thermal image;
    determine hot pixels of the thermal images belonging to a warm-bodied object by:
        subtracting the background image from the thermal images, and
        filtering out pixels of the thermal images being below a thermal threshold from the background image;
    record an estimation of a user's hand-wash motions, the user's hand-wash motions being estimated by determining a change in the hot pixels between the initial thermal image and the subsequent thermal image;
    estimate hand-wash scrubs per minute based on the user's hand-wash motions;

count a total hand-wash scrubs based on the user's hand-wash motions;
estimate hand-wash vigor based on a number of transitions between high and low motions;
calculate a hand-wash score based on the hand-wash vigor;
display the hand-wash vigor, the total hand-wash scrubs, and the hand-wash scrubs per minute on a display;
display a timer that counts down based on the hand-wash vigor; and
update the background image based on the warm-bodied object being absent from the thermal images.

12. The non-transitory computer readable medium of claim 11, wherein the instructions configured to display the hand-wash vigor includes the instructions configured to:
display a minimum vigor compliance indicator in red,
display a high vigor compliance indicator in yellow,
display a highest vigor compliance indicator in green; or
display a combination thereof.

13. The non-transitory computer readable medium of claim 11, wherein the instructions configured to calculate a hand-wash score based on the hand-wash vigor includes the instructions configured to:
decrease the hand-wash score based on the hand-wash vigor being estimated as a minimum vigor compliance;
increase the hand-wash score based on the hand-wash vigor being estimated as a high vigor compliance; and
increase the hand-wash score, based on the hand-wash vigor being estimated as a highest vigor compliance, and the increase based on the hand-wash vigor being estimated as the highest vigor compliance being faster than the hand-wash score increased based on the hand-wash vigor being estimated as the high vigor compliance.

14. The non-transitory computer readable medium of claim 11, wherein the instructions configured to display the timer that counts down based on the hand-wash vigor includes the instructions configured to pause the timer when the hand-wash vigor is estimated to be below a threshold.

15. The non-transitory computer readable medium of claim 11, further comprising instructions configured to:
determine a high score based on the hand-wash score for: a prior day, a prior week, a prior month, a prior year, and all time; and
display the high score for: the prior day, the prior week, the prior month, the prior year, and all time only when a full time period of the determination of the high score has elapsed.

16. The non-transitory computer readable medium of claim 11, further comprising instructions configured to display options to: add a user, delete the user, view the user's historical data, view multiple users, and view use and compliance statistics.

17. The non-transitory computer readable medium of claim 11, further comprising instructions configured to:
display the total hand-wash scrubs counted for each day of a current week; and
display the hand-wash score calculated for each of the days of the current week.

18. The non-transitory computer readable medium of claim 11, further comprising instructions configured to:
display multiple users in rows; and
display a role, the hand-wash scrubs per minute, the total hand-wash scrubs, and the hand-wash score for each of the multiple users.

19. The non-transitory computer readable medium of claim 11, further comprising instructions configured to display statistical calculations of the hand-wash scrubs per minute, the total hand-wash scrubs, the hand-wash vigor, the hand-wash score, the timer, or a combination thereof.

20. The non-transitory computer readable medium of claim 11, wherein the instructions configured to display the hand-wash vigor, the total hand-wash scrubs, and the hand-wash scrubs per minute, and the timer includes displaying the hand-wash vigor, the total hand-wash scrubs, and the hand-wash scrubs per minute, and the timer only after a user has been detected to be within a vicinity of a sensor.

* * * * *